(12) United States Patent
Whitehead

(10) Patent No.: US 7,666,608 B2
(45) Date of Patent: *Feb. 23, 2010

(54) METHODS FOR DETERMINING DRUG RESPONSIVENESS

(75) Inventor: Alexander Steven Whitehead, Wayne, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/463,846

(22) Filed: May 11, 2009

(65) Prior Publication Data

US 2009/0286267 A1 Nov. 19, 2009

Related U.S. Application Data

(63) Continuation of application No. 10/348,346, filed on Jan. 22, 2003, now abandoned.

(60) Provisional application No. 60/370,008, filed on Apr. 3, 2002.

(51) Int. Cl.
 G01N 33/53 (2006.01)
 G01N 33/00 (2006.01)
 C07K 14/00 (2006.01)
 C07H 21/02 (2006.01)
 C07D 215/04 (2006.01)

(52) U.S. Cl. .................. 435/7.1; 435/7.92; 435/7.24; 530/350; 536/23.1; 540/2

(58) Field of Classification Search ................. None
See application file for complete search history.

(56) References Cited

U.S. PATENT DOCUMENTS

| 5,744,304 | A | 4/1998 | Munford |
| 5,851,822 | A | 12/1998 | Munford |
| 6,300,085 | B1 | 10/2001 | Alkon |
| 6,878,518 | B2 | 4/2005 | Whitehead |

FOREIGN PATENT DOCUMENTS

WO WO97/04317 2/1997

OTHER PUBLICATIONS

Arenander et al., 1981, Brain Res. 224(1):105-16.
Arnett-Mansfield et al., 2001, Cancer Res. 61(11):4576-82.
Baumann et al., 1990, J Biol Chem 265(36):22275-22281.
Bausserman, et al., 1983, J Biol Chem.258(17):10681-8.
Bell et al., 1996, Scand J Immunol 43:173-180.
Butler et al., 1996,Immunogenetics 44:468-474.
Butler et al., 1997, Scand J. Immunol 45:160-165.
Carnec, et al., 2005 J Virol. 79(3):1930-3.
Celis et al., 2000, FEBS Lett 480:2-16.
Chen 2002, Mol Cell Proteomics. 1(4):304-13.
Chen, et al., 2001, J. Biol. Chem., 276(42):38628-38635.
Chikanza et al., 1993, Eur J Clin Invest 23:845-850.
Cohen et al., 1999, J Neuroimmunol 98:29-36.
Cunnane et al., 1999, Baillieres Best Pract Res Clin Rheumatol. 13(4):615-28.
Cunnane et al., 2000, J Rheumatol.27(1):58-63.
Ganapathi et al., 1991, J Immunol 147:1261-1265.
Gaughan et al., 1995, FEBS Lett 374:241-245.
Gaughan et al., 1997, Scand J Immunol 46:51-58.
Grehan et al., 1997, Eur J Immunol 27:2593-2599.
Grehan et al., 1997, J Immunol 159(1):369-378.
Gruber et al., 2004, Trends Endocrinol Metab. 15(2):73-8.
Hanauer et al., 1997, Am J Gastroenterol. 92(4):559-66.
Haynes et al., 1998, Electrophoresis 19:1862-1871.
Henrickse et al., 1979, Br Med J. 1(6159):306.
Huang et al., 1997, Breast Cancer Res Treat. 42(1):73-81.
Ito et al., 1999, J Immunol 162:4260-4265.
Jain et al., 1989 Indian J Chest Dis Allied Sci. 31(4):271-4.
Jensen et al., 1997, J Immunol. 158(1):384-92.
Jensen et al., 1998, Biochem J 334:489-503.
Jensen et al., 1998, J Immunol Methods. 215(1-2):45-58.
Jorgensen et al., 2000, Dev Comp Immunol. 24(6-7):553-63.
Kaplan et al., 1997, J Chromatogr B Biomed Sci Appl. 704(1-2):69-76.
Kluve-Beckerman, et al., 1988, J Clin Invest. Nov. 1988;82(5):1670-5.
Kornbluth et al., 1997, Am J Gastroenterol. 92(2):204-11.
Longley et al., 1999, J Immunol. 163(8):4537-45.
Madoz-Gurpide et al., 2003, Adv Exp Med Biol. 532:51-8.
McCormack et al., 1996, J Immunol Methods.198(1):101-10.
Nickerson et al., 1990, Proc Natl Acad Sci USA 87(22):8923-8927.
O'Hara et al., 2000, Arthritis Res 2(2):142-144.
O'Mahoney et al., 1996, Aliment Pharm Ther 10:671-680—Abstract.
Present 2000, Inflamm Bowel Dis 6(1):48-57(discussion 58).
Rebuck 1986, Eur J Respir Dis Suppl. 147:105-9.
Rygg et al., 2001, Scand J Immunol 53:588-595.
Saile, et al., 1988, Clin Chem. 34(9):1767-71.
Scheidereit et al., 1983, Nature, 304(5928):749-752.
Spitz et al., 1989, J Reprod Fertil Suppl. 37:253-60.
Steel et al., 1996, Scand J Immunol. 44(5):493-500.
Steiner et al., 2000, Electrophoresis 21:2099-2014.
Tobe et al., 1996, Nucleic Acids Res.24(19):3728-32.
Uhlar et al., 1996, Scand J Immunol. 43(3):271-6.
Uhlar et al., 1997, J Immunol Methods. 203(2):123-30.
Uhlar et al., 1999, Eur J Biochem 265:501-523.
Uhlar et al., 1999, Scand J Immunol. 49(4):399-404.
Urieli-Shoval et al., 1998, J Histochem Cytochem. 46(12):1377-84.
Woo, et al., 1987, J Biol Chem. 262(32):15790-5.
Yap et al., 1999, J Am Soc Nephrol 10:529-537.

*Primary Examiner*—Jeffrey Stucker
*Assistant Examiner*—Aditi Dutt
(74) *Attorney, Agent, or Firm*—Drinker Biddle & Reath LLP

(57) ABSTRACT

The invention provides a diagnostics assay for measuring the responsiveness to a drug by comparing the protein levels of a gene that responds to the drug, such as a steroid, to the protein levels of a gene that does not respond to the drug. Methods according to the invention are useful for predicting the ability of a patient (or a tissue, body fluid or cell sample in vitro) to respond to a drug or steroid at any stage of their treatment (i.e., before, during or after), and to monitor the patient (or a tissue, body fluid or cell) over time to assess continued responsiveness to the drug or steroid.

14 Claims, 10 Drawing Sheets

FIG. 1

|        | FIG. 1A |
|--------|---------|
|        | FIG. 1B |

FIG. 1A

```
            YY-1                                                  AP-1
SAA1  --TAGATATG AACTCAGAGG GACTTCATTT CAGAGGCATC TGCCATGTGG -391
SAA2  TTTAGACATG AACTCACAGG GATTTCAGT- CAGGGTCATC TGCCATGTGG -397
       *  ****** ********** ** ***  *  *** * **** **********
            AP-2             NFIL-6/YY-1
SAA1  CCCAGCAGAG CCCATCCTGA GGAAATGACT GGTAGAGTCA GGAGCTGGCT -341
SAA2  CCCAGCAGGG CCCATCCTGA GGAAATGACC GGTATAGTCA GGAGCTGGCT -347
      ********** ********** ********** **** ***** **********
                                                           YY-1
SAA1  TCAAAGCTGC CCTCACTTCA CACCTTCCAG CAGCCCAGGT GCCGCCATCA -291
SAA2  GAAGAGCTGC CCTCACTCCA CACCTTCCAG CAGCCCAGGT GCCGCCATCA -297
       * ******* ******* ** ********** ********** **********
          NFκB                           AP-2     SAF
SAA1  CGGGGCTCCC ACTCTCAACT CCGCAGCCTC AGCCCCCTCA ATGCTGAGGA -241
SAA2  CGGGGCTCCC ACTGGCATCT CTGCAGCTGC ACTTCCCCCA ATGCTGAGGA -247
      ************ *  **  * * **** *  * * ****** **********
      -240
```

FIG. 1A

```
SAA1  GCAGAGCTGG TCTCCTGCCC TGACAGCTGC CA-GGCACA- ------TC -201
SAA2  GCAGAGCTGA TCTAGCACCC TGTCCATTGC CAAGGCACAG CAAACCTCTC -197
      ******* ***  ***  **  ** *******  **
      -200 GRE                          AP-1

SAA1  TTGTTCCCTC AGGTTGCACA ACTGGGATAA ATGA CCCGGG  ATGAAGAAAC -151
SAA2  TTGTTCCCAT AGGTTACACA ACTGGGATAA ATGA CCCGGG  ATGAAGAAAC -147
      ******* **  ***** ****  **********  ****  ******  **********
      -150      NF-IL6/STAT                                YY-1

SAA1  CACTGGCATC CAGGAACTTG TCTTAGACCG TTTTGTAGGG GAAATGACCT -101
SAA2  CACCGGCATC CAGGAACTTG TCTTAGACCA GTTTGTAGGG GAAATGACCT -97
      *** ****** **********  *********   ********* **********
      -100 NFkB           SP-1

SAA1  GCAGGGACTT TCCCCAGGGA CCACATCCAG CTTTCTTCC  CTCCCAAGAA -51
SAA2  GCAGGGACTT TCCCCAGGGA CCACATCCAG CTTTCTTCC  CTCCCAAGAG -47
      **********  **********  **********  *********  *********
      -50

SAA1  ACCAGCAGGG AAGGCTCAGT ATAAATAGCA GCCACCGCTC CCTGGCAGGC -1
SAA2  ACCAGCA--- -AGGCTCACT ATAAATAGCA GCCACCTCTC CCTGGCAGAC -1
      *******     ****** ** **********  ******  **  ********  *
```

FIG. 1B

```
SAA1           CA-GGCACA------TCTTGTTCCCTCAGGTTGCACA
GREI           CA-GGCACAGCAAACCTCTCTTGTTCCCTCAGGTTGCACA
GRED           CAAGGCACA------TCTTGTTCCCATAGGTTACACA
SAA2           CAAGGCACAGCAAACCTCTCTTGTTCCCATAGGTTACACA
Consensus      GGTACA         NNNTGTTCT
GRE
```

FIG. 7A

| | |
|---|---|
| SAA1 | CAGACAAATACTTCCATGCTCGGGGAACTATGATGCTGCCAAAAGGGGACCTGGGGGTG 246 |
| SAA2 | CAGACAAATACTTCCATGCTCGGGGAACTATGATGCTGCCAAAAGGGGACCTGGGGGTG 246 |
| | exon3 exon4 |
| SAA1 | TCTGGGCTGCAGAAGGCGATCAG\|CGATG—//—//——TGAGCTTCCTCTTCACTCTGCTC 426 |
| SAA2 | CCTGGGCCGCAGAAGTGATCAG\|CAATG—//—//——TGAGCTTCCTCTTCACTCTGCTC 472 |
| SAA1 | TCAGGAGATCTGGCTGTGAGGC-TCAGGGCAGGATACAAAGC————GGGG———————— 486 |
| SAA2 | TCAGGAGACCTGGCTATGAGCCCTCGGGCAGGATTCAAAGTTAGTGAGTCTATGTCC 486 |
| SAA1 | AGAG————————GGTACACAATGGGTATCTAATAAATACTTAAGAGTGGAAAAAA 520 |
| SAA2 | AGAGAAGCTGAGAGATATGGCATATATAATAGGCATCTAATAAATGCTTAAGAGTGGAAAAAA 546 |

FIG. 8A

SEQUENCE LISTING

```
<160> NUMBER OF SEQ ID NOS: 29

<210> SEQ ID NO 1
<211> LENGTH: 15
<212> TYPE: DNA
<213> ORGANISM: Artificial Sequence
<220> FEATURE:
<223> OTHER INFORMATION: Glucocorticoid Responsive Element GRE consensus
      sequence
<220> FEATURE:
<221> NAME/KEY: n
<222> LOCATION: (7)..(9)
<223> OTHER INFORMATION: any nucleotide (A, G, C or T)
<220> FEATURE:
<221> NAME/KEY: misc_feature
<222> LOCATION: (7)..(9)
<223> OTHER INFORMATION: n is a, c, g, or t

<400> SEQUENCE: 1
ggtacannnt gttct                                                         15

<210> SEQ ID NO 2
<211> LENGTH: 438
<212> TYPE: DNA
<213> ORGANISM: Homo sapiens

<400> SEQUENCE: 2
tagatatgaa ctcagaggga cttcatttca gaggcatctg ccatgtggcc cagcagagcc        60
catcctgagg aaatgactgg tagagtcagg agctggcttc aaagctgccc tcacttcaca       120
ccttccagca gcccaggtgc cgccatcacg gggctcccac tctcaactcc gcagcctcag       180
```

| | |
|---|---|
| cccectcaat gctgaggagc agagctggtc tcctgccctg acagctgcca ggcacatctt | 240 |
| gttccctcag gttgcacaac tgggataaat gacccgggat gaagaaacca ctggcatcca | 300 |
| ggaacttgtc ttagaccgtt ttgtagggga aatgacctgc agggactttc cccagggacc | 360 |
| acatccagct tttcttccct cccaagaaac cagcagggaa ggctcagtat aaatagcagc | 420 |
| caccgctccc tggcaggc | 438 |

<210> SEQ ID NO 3
<211> LENGTH: 445
<212> TYPE: DNA
<213> ORGANISM: Homo sapiens

<400> SEQUENCE: 3

| | |
|---|---|
| tttagacatg aactcacagg gatttcagtc agggtcatct gccatgtggc ccagcagggc | 60 |
| ccatcctgag gaaatgaccg gtatagtcag gagctggctg aagagctgcc ctcactccac | 120 |
| accttccagc agcccaggtg ccgccatcac ggggctccca ctggcatctc tgcagctgca | 180 |
| cttcccccaa tgctgaggag cagagctgat ctagcaccct gtccattgcc aaggcacagc | 240 |
| aaacctctct tgttcccata ggttacacaa ctgggataaa tgacccggga tgaagaaacc | 300 |
| accggcatcc aggaacttgt cttagaccag tttgtagggg aaatgacctg cagggacttt | 360 |
| ccccagggac cacatccagc ttttcttccc tcccaagaga ccagcaaggc tcactataaa | 420 |
| tagcagccac ctctccctgg cagac | 445 |

<210> SEQ ID NO 4
<211> LENGTH: 87
<212> TYPE: DNA
<213> ORGANISM: Homo sapiens

<400> SEQUENCE: 4

| | |
|---|---|
| cagacaaata cttccatgct cgggggaact atgatgctgc caaaagggga cctgggggtg | 60 |
| tctgggctgc agaagcgatc agcgatg | 87 |

<210> SEQ ID NO 5
<211> LENGTH: 117
<212> TYPE: DNA
<213> ORGANISM: Homo sapiens

<400> SEQUENCE: 5

| | |
|---|---|
| tgagcttcct cttcactctg ctctcaggag atctggctgt gaggctcagg gcagggatac | 60 |
| aaagcgggga gagggtacac aatgggtatc taataaatac ttaagaggtg gaaaaaa | 117 |

<210> SEQ ID NO 6
<211> LENGTH: 87
<212> TYPE: DNA
<213> ORGANISM: Homo sapiens

<400> SEQUENCE: 6

| | |
|---|---|
| cagacaaata cttccatgct cgggggaact atgatgctgc caaaagggga cctgggggtg | 60 |
| cctgggccgc agaagtgatc agcaatg | 87 |

<210> SEQ ID NO 7
<211> LENGTH: 143
<212> TYPE: DNA
<213> ORGANISM: Homo sapiens

<400> SEQUENCE: 7

| | |
|---|---|
| tgagcttcct cttcactctg ctctcaggag acctggctat gagccctcgg ggcagggatt | 60 | caaagttagt gaggtctatg tccagagaag ctgagatatg gcatataata ggcatctaat        120 aaatgcttaa gaggtggaaa aaa        143

<210> SEQ ID NO 8
<211> LENGTH: 53
<212> TYPE: DNA
<213> ORGANISM: Artificial Sequence
<220> FEATURE:
<223> OTHER INFORMATION: PCR primer specific for human SAA2 gene

<400> SEQUENCE: 8
aagaattcac gcgtccatgc atgttgcggc cgcttggcca tcctttactt cct        53

<210> SEQ ID NO 9
<211> LENGTH: 49
<212> TYPE: DNA
<213> ORGANISM: Artificial Sequence
<220> FEATURE:
<223> OTHER INFORMATION: PCR probe specific for human SAA2 gene

<400> SEQUENCE: 9
ttgaattcct cgagcaggta ccatacatat gtagctgagc tgcgggtcc        49

<210> SEQ ID NO 10
<211> LENGTH: 42
<212> TYPE: DNA
<213> ORGANISM: Artificial Sequence
<220> FEATURE:
<223> OTHER INFORMATION: Forward PCR primer for human SAA1 gene

<400> SEQUENCE: 10
gaattcacgc gtttgggcag ggaatatact tatttatgga ag        42

<210> SEQ ID NO 11
<211> LENGTH: 42
<212> TYPE: DNA
<213> ORGANISM: Artificial Sequence
<220> FEATURE:
<223> OTHER INFORMATION: Reverse PCR primer for human SAA1 gene

<400> SEQUENCE: 11
gaattcccat ggtgctgatc tgtgctgtag ctgagctgcg gg        42

<210> SEQ ID NO 12
<211> LENGTH: 42
<212> TYPE: DNA
<213> ORGANISM: Artificial Sequence
<220> FEATURE:
<223> OTHER INFORMATION: Forward PCR primer for human SAA1 gene

<400> SEQUENCE: 12
gaattcacgc gtgcgtgatt atagctcact gcagccttga cc        42

<210> SEQ ID NO 13
<211> LENGTH: 25
<212> TYPE: DNA
<213> ORGANISM: Artificial Sequence
<220> FEATURE:
<223> OTHER INFORMATION: Forward PCR primer for human SAA1 gene

<400> SEQUENCE: 13
gaattcacgc gtggtctcct gcctg        25

<210> SEQ ID NO 14

```
<211> LENGTH: 32
<212> TYPE: DNA
<213> ORGANISM: Artificial Sequence
<220> FEATURE:
<223> OTHER INFORMATION: Forward PCR primer for human SAA2 gene

<400> SEQUENCE: 14
tataacgcgt cctatttaac gcaccacact ct                               32

<210> SEQ ID NO 15
<211> LENGTH: 25
<212> TYPE: DNA
<213> ORGANISM: Artificial Sequence
<220> FEATURE:
<223> OTHER INFORMATION: Forward PCR primer for human SAA2 gene

<400> SEQUENCE: 15
gaattcacgc gtgatctagc acctg                                      25

<210> SEQ ID NO 16
<211> LENGTH: 20
<212> TYPE: DNA
<213> ORGANISM: Artificial Sequence
<220> FEATURE:
<223> OTHER INFORMATION: PCR mutagenesis primer GRE1F

<400> SEQUENCE: 16
cagcaaacct ctcttgtccc                                            20

<210> SEQ ID NO 17
<211> LENGTH: 19
<212> TYPE: DNA
<213> ORGANISM: Artificial Sequence
<220> FEATURE:
<223> OTHER INFORMATION: PCR mutagenesis primer GRE1R

<400> SEQUENCE: 17
agagaggttt gctgtgcct                                             19

<210> SEQ ID NO 18
<211> LENGTH: 25
<212> TYPE: DNA
<213> ORGANISM: Artificial Sequence
<220> FEATURE:
<223> OTHER INFORMATION: PCR mutagenesis primer GREDF

<400> SEQUENCE: 18
caaggcacat cttgttccca taggt                                      25

<210> SEQ ID NO 19
<211> LENGTH: 24
<212> TYPE: DNA
<213> ORGANISM: Artificial Sequence
<220> FEATURE:
<223> OTHER INFORMATION: PCR mutagenesis primer GREDR

<400> SEQUENCE: 19
ggaacaagat gtgccttggc aatg                                       24

<210> SEQ ID NO 20
<211> LENGTH: 20
<212> TYPE: DNA
<213> ORGANISM: Artificial Sequence
<220> FEATURE:
<223> OTHER INFORMATION: RT-PCR forward primer

<400> SEQUENCE: 20
```
cagacaaata cttccatgct                                         20

<210> SEQ ID NO 21
<211> LENGTH: 29
<212> TYPE: DNA
<213> ORGANISM: Artificial Sequence
<220> FEATURE:
<223> OTHER INFORMATION: Reverse RT-PCR primer

<400> SEQUENCE: 21 tttttccac ctcttaagta tttattaga                                29

<210> SEQ ID NO 22
<211> LENGTH: 29
<212> TYPE: DNA
<213> ORGANISM: Artificial Sequence
<220> FEATURE:
<223> OTHER INFORMATION: Reverse RT-PCR primer

<400> SEQUENCE: 22 tttttccac ctcttaagca tttattaga                                29

<210> SEQ ID NO 23
<211> LENGTH: 15
<212> TYPE: DNA
<213> ORGANISM: Homo sapiens

<400> SEQUENCE: 23
ggcacatctt gttcc                                              15

<210> SEQ ID NO 24
<211> LENGTH: 104
<212> TYPE: PRT
<213> ORGANISM: Homo sapiens

<400> SEQUENCE: 24

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Val Trp Ala Ala Glu Ala Ile Ser Asp Ala Arg Glu Asn
    50                  55                  60

Ile Gln Arg Phe Phe Gly His Gly Ala Glu Asp Ser Leu Ala Asp Gln
65                  70                  75                  80

Ala Ala Asn Glu Trp Gly Arg Ser Gly Lys Asp Pro Asn His Phe Arg
                85                  90                  95

Pro Ala Gly Leu Pro Glu Lys Tyr
            100

<210> SEQ ID NO 25
<211> LENGTH: 104
<212> TYPE: PRT
<213> ORGANISM: Homo sapiens

<400> SEQUENCE: 25

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

```
Asp Lys Tyr Phe His Ala Arg Gly Asn Tyr Asp Ala Ala Lys Arg Gly
            35                  40                  45

Pro Gly Gly Ala Trp Ala Ala Glu Val Ile Ser Asn Ala Arg Glu Asn
         50                  55                  60

Ile Gln Arg Leu Thr Gly His Gly Ala Glu Asp Ser Leu Ala Asp Gln
 65                  70                  75                  80

Ala Ala Asn Lys Trp Gly Arg Ser Gly Arg Asp Pro Asn His Phe Arg
                 85                  90                  95

Pro Ala Gly Leu Pro Glu Lys Tyr
            100

<210> SEQ ID NO 26
<211> LENGTH: 30
<212> TYPE: DNA
<213> ORGANISM: Artificial Sequence
<220> FEATURE:
<223> OTHER INFORMATION: The region of SAA1 promoter encompassing GRE

<400> SEQUENCE: 26
caggcacatc ttgttccctc aggttgcaca                                   30

<210> SEQ ID NO 27
<211> LENGTH: 39
<212> TYPE: DNA
<213> ORGANISM: Artificial Sequence
<220> FEATURE:
<223> OTHER INFORMATION: The mutant GREI

<400> SEQUENCE: 27
caggcacagc aaacctctct tgttccctca ggttgcaca                         39

<210> SEQ ID NO 28
<211> LENGTH: 31
<212> TYPE: DNA
<213> ORGANISM: Artificial Sequence
<220> FEATURE:
<223> OTHER INFORMATION: The mutant GRED

<400> SEQUENCE: 28
caaggcacat cttgttccca taggttacac a                                 31

<210> SEQ ID NO 29
<211> LENGTH: 40
<212> TYPE: DNA
<213> ORGANISM: Artificial Sequence
<220> FEATURE:
<223> OTHER INFORMATION: The region of SAA2 encompassing the GRE

<400> SEQUENCE: 29
caaggcacag caaacctctc ttgttcccat aggttacaca                        40
```

METHODS FOR DETERMINING DRUG RESPONSIVENESS

CROSS-REFERENCE TO RELATED APPLICATIONS

This application is a continuation application of U.S. patent application Ser. No. 10/348,346, filed Jan. 22, 2003, (now abandoned) and claims the benefit of U.S. patent application Ser. No. 10/045,360, filed Jan. 22, 2002, (now issued as U.S. Pat. No. 6,878,518) and U.S. Provisional Application Ser. No. 60/370,008, filed Apr. 3, 2002, the disclosures of which are incorporated herein by reference in their entirety.

FIELD OF THE INVENTION

The invention relates to a diagnostic assay for drug (e.g., steroid) responsiveness.

BACKGROUND OF THE INVENTION

Many diseases that are primarily inflammatory in nature, (for example, rheumatoid arthritis, inflammatory bowel diseases, systemic lupus erythematosis, and asthma) or that have a major inflammatory component, are treated with steroids such as prednisone. In addition, some cancers are treated with steroids, and transplant patients also receive steroids to prevent transplant rejection. However, the effectiveness of steroid treatment varies from patient to patient and is usually impossible to predict. Some patients may be constitutively non-responsive to a particular medication, and others may become refractory to treatment over time. In some cases, patients may experience symptomatic relief, but attempts to withdraw therapy lead to disease flare. As a consequence, the inclination for doctors to continue steroid therapy and even to increase the dosage of a steroid is associated with serious, cumulatively debilitating, side effects. The clinical screening of patients who are candidates for steroid therapy for their ability to respond to steroids and the monitoring of patients who are undergoing steroid therapy but who may be transitioning from steroid responder to non-responder (i.e., refractory) status is therefore of significant clinical importance.

A need therefore exists for a diagnostic assay or test for drug, e.g., steroid responsiveness.

SUMMARY OF THE INVENTION

The invention provides diagnostic assays for measuring the response to a drug by comparing mRNA levels expressed by a gene that is expected to respond to the drug to mRNA levels expressed by a gene that is not expected to respond to the drug. The assay also can be carried out at the protein level, by comparing the concentrations and/or activities (for example enzymatic activities) of the proteins corresponding to these mRNA species. The invention is based on observations that the expression of drug-sensitive genes, or changes in the expression of drug-sensitive genes, are useful as a marker for the cellular response to the drug. Methods according to the invention are useful for predicting the ability of a patient (or a tissue, body fluid or cell sample in vitro) to respond to a treatment before treatment begins and to monitor treatment over time to assess continued responsiveness to therapeutic intervention.

In one aspect, the invention provides methods for determining steroid responsiveness in a subject, by determining the level of expression of RNA (or the protein encoded by the RNA) from a first gene known or suspected to be steroid responsive, determining the level of expression of RNA (or the protein encoded by the RNA) from a second gene known or suspected to be non-responsive to steroids, and comparing the pre- and post-treatment levels to determine or predict whether the subject is likely to respond to steroid treatment. The subject is determined or predicted to be steroid responsive if the change in the level of mRNA or protein expression from the first gene is higher than that from the second gene and the subject is non-responsive to steroids if the level of mRNA or protein expression from the second gene is equal to or higher than that from the first gene. Alternatively, the ratio of the expression from the first gene to the expression from the second gene may be compared to predetermined control ratios from untreated subjects or to predetermined control ratios from subjects undergoing successful treatment. For example, a subject may be predicted to be steroid responsive if the ratio of the expression from the steroid responsive gene to the expression of the steroid non-responsive gene is similar to prior ratios for the subject when previously responsive or higher than the predetermined control ratio for untreated subjects or similar to predetermined control ratios from subjects undergoing successful treatment. Conversely, the subject may be predicted to be steroid non-responsive if the ratio of the expression of the steroid responsive gene to the expression of the steroid non-responsive gene is lower than prior ratios for the subject when previously responsive, or similar to the predetermined control ratio for untreated subjects, or lower than predetermined control ratios from subjects undergoing successful treatment.

In another embodiment, the invention provides methods for determining steroid responsiveness in a tissue, body fluid or cell after exposure in vitro to a steroid.

In another embodiment, the invention provides methods for determining or predicting steroid responsiveness in a subject before and after (i.e., following or during administration of) steroid treatment. Samples are taken before and after steroid treatment, and the RNA (or protein) levels for the steroid non-responsive gene are used as a normalizing control for the RNA (or protein) levels of the steroid responsive gene. The invention provides for: (i) obtaining a pre-treatment tissue, body fluid or cell from a subject, (ii) determining the level of RNA or protein expression from steroid responsive and steroid non-responsive genes, (iii) administering a steroid to the subject, (iv) obtaining a post-treatment tissue, body fluid or cell from the subject and (v) determining a post-treatment RNA or protein level expressed from the same genes identified in the pre-treatment samples, (vi) comparing the pre-treatment level of RNA or protein expressed from the first gene to the pre-treatment level of RNA or protein expressed from the second gene to create a first normalized value, comparing the post-treatment level of RNA or protein expressed from the first gene to the post-treatment level of RNA or protein expressed from the second gene to create a second normalized value, and comparing the first normalized value to the second normalized value. If the first normalized value is less than the second normalized value, the tissue, body fluid or cell sample is predicted or determined to be steroid responsive and if the first normalized value is greater than or the same as the second normalized value the tissue, body fluid or cell sample is predicted or determined to be steroid non-responsive. The difference between the first normalized value and the second normalized value correlates to the ability of the subject to respond to steroid treatment.

In another embodiment, the invention provides methods for determining an effective dose of a steroid in a subject by administering to a subject a dose of a steroid, obtaining a tissue, body fluid or cell sample from the subject, determining the level of expression of RNA or protein from a first gene known or suspected to be steroid responsive, determining the level of expression of RNA or protein from a second gene known or suspected to be non-responsive to steroids, and comparing the pre- and post-treatment levels to determine whether the dose of steroid is appropriate. Alternatively, the ratio of the expression from the first gene to the expression from the second gene is compared to predetermined control ratios from untreated subjects. This alternative allows for the continued assessment of effective dosage during a course of treatment if no pre-treatment sample is available, e.g., in the case of a chronic condition. For example, a subject may be receiving an adequate dosage of steroid if the ratio of the expression from the first gene to the expression from the second gene is higher than the predetermined control ratio for untreated subjects. The dosage may be titrated or lowered until just before the ratio of RNA or protein levels from the steroid responsive to steroid non-responsive gene begins to decrease, in order to determine the minimum dosage that can be given to achieve optimal results. Alternatively, a subject may be given an initial low dose of steroid, the ratio of RNA or protein levels from the steroid responsive to steroid non-responsive gene measured, and the dosage increased until the ratio reaches a plateau, or until the ratio reaches a desired target level.

In some cases a patient may be obtaining clinical benefit (e.g., symptomatic relief) from steroid therapy but later become refractory (i.e., non-responsive to the therapy). The instant invention provides methods for ensuring the long-term appropriateness and efficacy of a steroid treatment by monitoring a subject's ability to respond to the steroid. The invention provides methods for monitoring a subject's ability to respond to a steroid by administering to a subject a dose of steroid, obtaining a tissue, body fluid or cell sample from the subject, determining the level of expression of RNA or protein from a first gene known or suspected to be steroid responsive, determining the level of expression of RNA or protein from a second gene known or suspected to be non-responsive to steroids, and comparing them pre- and post-treatment to determine whether the subject is still responsive to steroid treatment. The subject remains steroid responsive if the level of expression from the steroid responsive gene is higher than that of the steroid non-responsive gene and the subject has become non-responsive to steroids if the level of expression from the steroid non-responsive gene is equal to or higher than that of the steroid responsive gene. Alternatively, the ratio of the expression from the steroid responsive gene to the expression from the steroid non-responsive gene is compared to predetermined control ratios from untreated subjects or to predetermined control ratios from subjects undergoing successful treatment or to a preexisting ratio from the subject obtained at a time when the subject was classified as steroid responsive. For example, a subject may be steroid responsive if the ratio of the expression from the steroid responsive gene to the expression of the steroid non-responsive gene is similar to prior ratios for the subject when previously responsive or higher than the predetermined control ratio for untreated subjects or similar to predetermined control ratios from subjects undergoing successful treatment. Conversely, the subject may be steroid non-responsive if the ratio of the expression from the steroid responsive gene to the expression of the steroid non-responsive gene is lower than prior ratios for the subject when previously responsive or similar to the predetermined control ratio for untreated subjects or lower than predetermined control ratios from subjects undergoing successful treatment.

More generally, the invention also provides a general approach to determining drug responsiveness generally in a subject undergoing drug treatment. In this method a first gene must be identified which responds to the drug by causing a change in RNA or protein production (e.g., change in transcription, RNA stability, or RNA accumulation). A second gene must also be identified which does not respond to the drug by causing a change in RNA or protein production. In another aspect, the invention provides methods for determining drug responsiveness in a subject undergoing drug treatment by determining the level of expression of RNA or protein from a first gene known or suspected to be drug-responsive, determining the level of expression of RNA or protein from a second gene known or suspected to be non-responsive to the drug, and comparing them pre- and post-treatment to determine whether the subject is likely to respond to drug treatment. The subject is determined to be drug-responsive if the level of expression from the drug-responsive gene is higher than that of the drug non-responsive gene and the subject is non-responsive to the drug if the level of expression from the drug non-responsive gene is equal to or higher than that of the drug-responsive gene. Alternatively, the ratio of the expression from the drug-responsive gene to the expression from the drug non-responsive gene is compared to predetermined control ratios from untreated subjects or to predetermined control ratios from subjects undergoing successful treatment. For example, a subject may be drug-responsive if the ratio of the expression from the drug-responsive gene to the expression of the drug non-responsive gene is similar to prior ratios for the subject when previously responsive or higher than the predetermined control ratio for untreated subjects or similar to predetermined control ratios from subjects undergoing successful treatment. Conversely, the subject may be drug non-responsive if the ratio of the expression from the drug-responsive gene to the expression of the drug non-responsive gene is lower than prior ratios for the subject when previously responsive or similar to the predetermined control ratio for untreated subjects or lower than predetermined control ratios from subjects undergoing successful treatment.

In another embodiment, the invention provides methods for determining drug responsiveness in a tissue, body fluid or cell after exposure in vitro to a drug.

In another embodiment, the invention provides methods for determining responsiveness in a tissue, body fluid or cell sample to a drug or drug candidate for determining alterations in the cellular response to pro-inflammatory, anti-inflammatory or immune response-modifying stimuli (e.g., cytokines, chemokines, steroids, etc.). In other words, the methods according to the invention may detect side effects of drugs on immune responses in cells. The cellular response may be assessed by comparing the relative levels of endogenous steroid responsive gene and steroid nonresponsive gene mRNA or protein, as described herein. Alternatively, cells may be transfected with a vector or vectors having the steroid responsive gene and steroid nonresponsive gene promoters, each in operative linkage with a different detectable reporter gene (e.g., green fluorescence protein or yellow fluorescence protein). The method includes exposing the cell, transfected with the vector(s) having the steroid responsive gene and steroid nonresponsive gene promoter-driven reporter genes, to a drug of interest and comparing the level of expression from the first reporter gene to the level of expression from the second reporter gene. In this way, a drug that may or may not have pro- or anti-inflammatory or immune response-modifying activity can be assayed for its effect on gene expression from the steroid responsive gene and steroid nonresponsive gene promoters.

In a particular embodiment, RNA levels are quantified by amplification of the RNA by, for example, reverse transcription polymerase chain reaction (RT-PCR) of the RNAs. The reaction products may be quantified, e.g., by gel electrophoresis (e.g., slab or capillary) or the unamplified RNA may be quantified, e.g., by Northern blot analysis, or by direct hybridization with a probe. Alternatively, RNA levels are quantified by in situ detection. Diagnostic procedures may also be performed in situ directly upon sections (fixed or frozen) of tissue obtained from biopsies or resections by looking at relative intensities of drug or steroid responsive and drug or steroid nonresponsive RNAs in a portion of the biopsy sample, such that no nucleic acid purification is necessary. Nucleic acid reagents may be used as probes and/or primers for such in situ procedures.

In another embodiment, the relative changes in gene expression may be quantified at the protein level. An analysis of gene expression may therefore be directed at the quantity of a particular mRNA transcript or the amount of protein translated from it, or the activity of that protein. Protein levels may be quantified using well-known techniques of protein analysis. For example, target tissue is first isolated and then total protein is extracted by well known methods. Quantitative analysis is achieved, for example, using ELISA methods employing a pair of antibodies specific to the target protein. Other methods of protein quantification include enzymatic assay, use of biosensors, protein arrays or protein chips, for example, the chips available from Ciphergen (Fremont, Calif.), and mass spectrometric methods as described in more detail below. The skilled artisan will recognize that any protein quantification method that is specific for a given protein may be used in the instant methods.

RNA or protein may be quantified from any tissue, body fluid or nucleated cell sample. For example, the tissue or body fluid sample is preferably blood. The tissue sample may be derived from a biopsy of any tissue in which the genes of interest (i.e., the drug or steroid responsive gene and the drug or steroid non-responsive gene) are expressed. The tissue, body fluid or cell sample may contain one or more of monocytes, macrophages, neutrophils, T-cells, B-cells, basophils, fibroblasts, smooth muscle cells, endothelial cells and epithelial cells, for example. In addition, the tissue or cell sample may be a benign tumor, malignant tumor, a tissue that is normally responsive to steroids (such as a breast cancer biopsy sample, e.g., to determine whether it has lost the ability to respond to steroids, has become less responsive to steroids, or has become more responsive to steroids) or a tissue that is non-responsive to steroids (e.g., to determine if it has gained responsiveness to steroids). In a preferred embodiment, the tissue used to measure RNA levels of the genes of interest contains buccal cells. The tissue, body fluid or cell sample is obtained and is preferably stored in a stabilization solution or is stored frozen prior to analysis to minimize RNA or protein degradation.

In another embodiment of the invention, the methods involve the step of administering one or more pro-inflammatory or anti-inflammatory mediators to the tissue, body fluid or cell, such as interleukin 1α (IL-1α), interleukin-1β (IL-1β), interleukin 6 (IL-6), and tumor necrosis factor (TNF-α). In addition, the anti-inflammatory mediator may be interleukin 1 receptor antagonist (IL-1RA), tumor necrosis factor receptor antagonist (TNF-RA) or derivatives thereof, soluble TNF receptors, or anti-TNF antibodies, for example. Other suitable pro-inflammatory or anti-inflammatory mediators for use in the invention are known in the art. Methods according to the invention may involve the step of administering one or more cytokines, chemokines (e.g., interleukin-8 (IL-8)), interferons, or other hormones (e.g., vasoactive intestinal peptide (VIP)).

Although the methods according to the invention may be used to predict, determine, measure or monitor the responsiveness of a subject to any drug that may cause an increase in RNA or protein levels of at least one gene but that does not cause an increase in RNA or protein levels of at least one other gene, the assay is ideally suited for predicting, determining, measuring or monitoring the responsiveness of a subject to steroids.

In a preferred embodiment, differential cytokine-dependent or cytokine-independent transcriptional activities of the steroid responsive and steroid nonresponsive genes are used to measure steroid responsiveness in the presence or absence of glucocorticoids. Genes of particular interest for measuring steroid responsiveness are derived from the serum amyloid A (SAA) gene superfamily. One SAA gene, serum amyloid A1 (SAA1), is responsive to glucocorticoids both in vivo and in vitro, causing an increase in transcription of SAA1 RNA and a concomitant increase in SAA1 RNA levels. Another SAA gene, serum amyloid A2 (SAA2) is not responsive to glucocorticoids. Thus, a preferred steroid responsive gene according to the invention is SAA1 and a preferred steroid nonresponsive gene is SAA2. Alternatively, the steroid responsive gene may encode another acute phase reactant, chemokine, cytokine agonist, cytokine antagonist, complement component, or other gene that is responsive to steroids (i.e., steroid treatment causes an increase in RNA or protein levels). Accordingly, the steroid-non-responsive gene may encode an acute phase reactant, chemokine, cytokine agonist, cytokine antagonist, complement component, or other gene which is not responsive to steroids (i.e., steroid treatment does not cause an increase in RNA or protein levels).

SAA1 transcription, but not SAA2 transcription, is induced in response to steroids in the absence of cytokines in some cell types (e.g., oral epithelial). Other cell types (e.g., HEPG2 hepatoma) require the presence of endogenous (e.g., due to ongoing inflammation), or exogenously administered cytokines, to achieve induction of SAA1 and SAA2 transcription which permits a subsequent or coincident steroid-dependent transcriptional enhancement of the SAA1 but not the SAA2 gene. Cell types which do not require such exposure to endogenous or exogenous cytokines are particularly useful for determining steroid responsiveness in a non-inflamed individual (e.g., a pre-surgery, pre-transplantation, or pre-treatment patient).

In another preferred embodiment, the methods according to the invention may be used to evaluate steroid responsiveness in response to the administration of a combination of stimuli or drugs, such as one or more of IL-1, IL-6 and TNF-α, and may thereby be useful in evaluating therapies under a range of inflammation conditions and/or treatment modalities. For example, the steroid responsive and non-responsive genes according to the methods of the invention may be chosen depending upon their ability to respond to IL-1 and IL-6, administered separately or in combination, with or without steroids. For example, both the SAA1 gene and SAA2 genes respond to IL-1 strongly and IL-6 weakly, but only the responses of the SAA1 gene are augmented by glucocorticoid administration. By comparison, the C reactive protein gene (CRP) responds weakly to IL-1 and strongly to IL-6, and both responses are augmented by glucocorticoid administration. The SAA genes and the CRP gene therefore are markers for subsets of genes that respond differentially to certain cytokines alone or in combination with steroids and/or other drugs. Thus, a comparison of the RNA or protein levels of the SAA genes and the CRP genes, and/or other genes, may provide useful RNA or protein profiles which predict, determine, measure or monitor a subject's ability to respond to steroids at certain points during an acute phase response (i.e., depending upon the "mix" of cytokines present at that point in time) or to certain cytokines, cytokine antagonists, anti-inflammatory or other drug treatments in the absence of, or in combination with, endogenous or exogenous (i.e., therapeutically administered) steroids.

Methods according to the invention may therefore further include the step of quantifying the RNA or protein level of a third gene, or additional genes, and comparing the RNA or protein level from the third or additional genes to the RNA or protein levels of the steroid responsive gene and the RNA or protein level of the steroid non-responsive gene. In a preferred embodiment, the third gene may encode an acute phase reactant, chemokine, cytokine agonist, cytokine antagonist, or complement component. Exemplary third genes are CRP, complement component 3 (C3), Factor B, or albumin.

Methods according to the invention are preferably used to predict, determine, measure or monitor the steroid responsiveness of a subject who suffers from an inflammatory condition, a disease with an inflammatory component, a disease with an inflammatory consequence, and/or a disease with inflammatory symptoms. The subject may be assayed to determine if he or she will respond to, will not respond to, is refractory to, is less responsive to, or is more responsive to steroid treatment, or is steroid dependent. Methods according to the invention are particularly useful for predicting, determining, measuring or monitoring the steroid responsiveness of a subject who suffers from an arthritic disease such as, for example, osteoarthritis, rheumatoid arthritis, psoriatic arthritis or idiopathic arthritis. Methods according to the invention are also useful for predicting, determining, measuring or monitoring the steroid responsiveness of a subject who suffers from an autoimmune disease, such as an inflammatory bowel disease (e.g., Crohn's disease or ulcerative colitis). Other diseases and conditions that have an inflammatory component or consequence include, but are not limited to, asthma, adult respiratory distress syndrome, systemic lupus erythematosus, multiple sclerosis, insulin-dependent diabetes mellitus, autoimmune arthritis, juvenile rheumatoid arthritis, psoriatic arthritis, inflammatory pulmonary syndrome, pemphigus vulgaris, idiopathic thrombocytopenic purpura, cerebral edema, autoimmune meningitis, myasthenia gravis, autoimmune thyroiditis, sarcoidosis, dermatitis, atopic dermatitis, eczematous dermatitis, psoriasis, Sjogren's Syndrome, sarcoidosis, keratoconjunctivitis sicca secondary to Sjogren's Syndrome, alopecia areata, allergic responses due to arthropod bite reactions, aphthous ulcer, iritis, conjunctivitis, keratoconjunctivitis, cutaneous lupus erythematosus, scleroderma, vaginitis, proctitis, drug eruptions, Stevens-Johnson syndrome, leprosy reversal reactions, erythema nodosum leprosum, autoimmune uveitis, allergic encephalomyelitis, aplastic anemia, pure red cell anemia, autoimmune destruction of erythrocytes, idiopathic thrombocytopenia, polychondritis, Wegener's granulomatosis, chronic active hepatitis, alcohol liver disease, Graves opthalmopathy, primary biliary cirrhosis, uveitis posterior and interstitial lung fibrosis.

Alternatively, methods according to the invention are used to determine steroid responsiveness in a subject who is being evaluated as a candidate for, is about to undergo, or has undergone a tissue or organ transplant. Alternatively, the subject has cancer, is being treated for cancer, or is in remission from cancer (e.g., solid tumors, acute lymphocytic leukemia and lymphoma). Alternatively, the subject suffers from or the assay is used to diagnose or monitor, a renal disease, allergy, infectious disease, ocular disease, skin disease, gastrointestinal disease, endocrine disease, stroke, coronary artery disease, vascular disease, atherothrombotic disease, spinal cord injury, acute adrenal insufficiency, chronic primary adrenal insufficiency, secondary adrenal insufficiency, and/or congenital adrenal hyperplasia. Alternatively, the subject is being evaluated as a candidate for, is about to undergo, or has undergone steroid replacement or substitution therapy.

In a preferred embodiment of the invention, the steroid responsive gene is controlled by a steroid responsive element, such as a glucocorticoid responsive element (GRE). The GRE may be a consensus GRE or a non-consensus GRE. The consensus GRE is preferably GGTACAnnnTGTTCT (SEQ ID NO:1), where n is any nucleotide (A, G, C or T), or a variation thereof. Alternatively, the first gene is controlled either in cis or in trans (e.g., in each case either proximally or distally) by a non-consensus element that permits the gene to respond to steroids. The steroid may provide a signal via the glucocorticoid receptor (GR) or via another steroid (e.g., estrogen, progesterone, etc.) receptor that may engage the GRE and/or another steroid response element in the steroid responsive gene, or at another genomic location. In a preferred embodiment, the steroid non-responsive gene is encoded by a gene which is not controlled by a steroid response element.

The steroid used in the methods according to the invention may be, for example, a glucocorticoid, an estrogen, or an androgen. Exemplary steroids include, but are by no means limited to, alclometasone diproprionate, amcinonide, beclomethasone diproprionate, betamethasone, betamethasone benzoate, betamethasone diproprionate, betamethasone sodium phosphate, betamethasone sodium phosphate and acetate, betamethasone valerate, clobetasol proprionate, clocortolone pivalate, cortisol (hydrocortisone), cortisol (hydrocortisone) acetate, cortisol (hydrocortisone) butyrate, cortisol (hydrocortisone) cypionate, cortisol (hydrocortisone) sodium phosphate, cortisol (hydrocortisone) sodium succinate, cortisol (hydrocortisone) valerate, cortisone acetate, desonide, desoximetasone, dexamethasone, dexamethasone acetate, dexamethasone sodium phosphate, diflorasone diacetate, fludrocortisone acetate, flunisolide, fluocinolone acetonide, fluocinonide, fluorometholone, flurandrenolide, halcinonide, medrysone, methylprednisolone, methylprednisolone acetate, methylprednisolone sodium succinate, mometasone furoate, paramethasone acetate, prednisolone, prednisolone acetate, prednisolone sodium phosphate, prednisolone tebutate, prednisone, triamcinolone, triamcinolone acetonide, triamcinolone diacetate, and triamcinolone hexacetonide or a synthetic analog thereof, or a combination thereof.

The invention further contemplates the administration of one or more steroid inhibitors or steroid antagonists. Exemplary steroid inhibitors include, but are not limited to, mitotane, metyrapone, aminoglutethimide, ketoconazole, and trilostane.

The steroid may be administered any number of ways, including, for example, parenterally, orally, locally, rectally, intravenously, topically, intramuscularly, enterally, transdermally, nasally, ocularly, transmucosally, via inhalation, and/or subcutaneously.

In another aspect, the invention provides a kit for determining drug (e.g., steroid) responsiveness in a subject where the kit contains a probe specific for, or primers specific for amplifying, RNA encoded by a drug-responsive gene and probes specific for, or primers specific for amplifying, RNA encoded by a drug non-responsive gene. Preferably, the kit also has a tissue, body fluid or cell collector. In a preferred embodiment, the collector contains RNase inhibitors and other inhibitors and preservatives for minimizing degradation of RNA and DNA. For example, a PAXgene™ Blood RNA tube (Qiagen, Hilden, Germany) may be used.

In a further aspect, the invention provides a kit for determining drug (e.g., steroid) responsiveness in a subject where the kit contains reagents suitable for detecting protein encoded by a drug-responsive gene and reagents suitable for detecting protein encoded by a drug non-responsive gene. Preferably, the kit also has a tissue, body fluid or cell collector. In a preferred embodiment, the collector contains protease inhibitors and other inhibitors and preservatives for minimizing degradation of the proteins e.g EDTA.

In yet another aspect, the invention provides methods for determining the capacity of a biological sample to induce the expression of SAA1 and/or SAA2 and/or any other inflammation-associated gene(s), or reporter constructs containing their promoters, in cultured primary and permanent cell lines. Such methods are useful for obtaining and monitoring an expression profile generated by a sample from a subject that is about to undergo, is undergoing, or has completed a therapy, as well as for providing a diagnostic or prognostic tool. The methods may also be used to assess the potential efficacy and side effects of investigational and approved drugs in biological samples, e.g., collected in the course of animal testing and/or Phase I, II, III, and IV clinical trials and/or post-marketing studies.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The foregoing and other objects, features and advantages of the present invention, as well as the invention itself, will be more fully understood from the following description of preferred embodiments when read together with the accompanying drawings, in which:

FIG. 1, comprising FIGS. 1A and 1B, is an alignment of SAA1 and SAA2 promoters. The proximal 450 bases of the human SAA1 and SAA2 promoters (SEQ ID Nos: 2 and 3) were aligned using the ClustalW program. Putative transcription factor binding sites are underlined once (predicted by TESS program), with dots (predicted by Signalscan program) or twice (predicted by visual inspection). Dashes represent gaps in one sequence relative to the other. The Xma1 site is boxed.

Figure 2A:
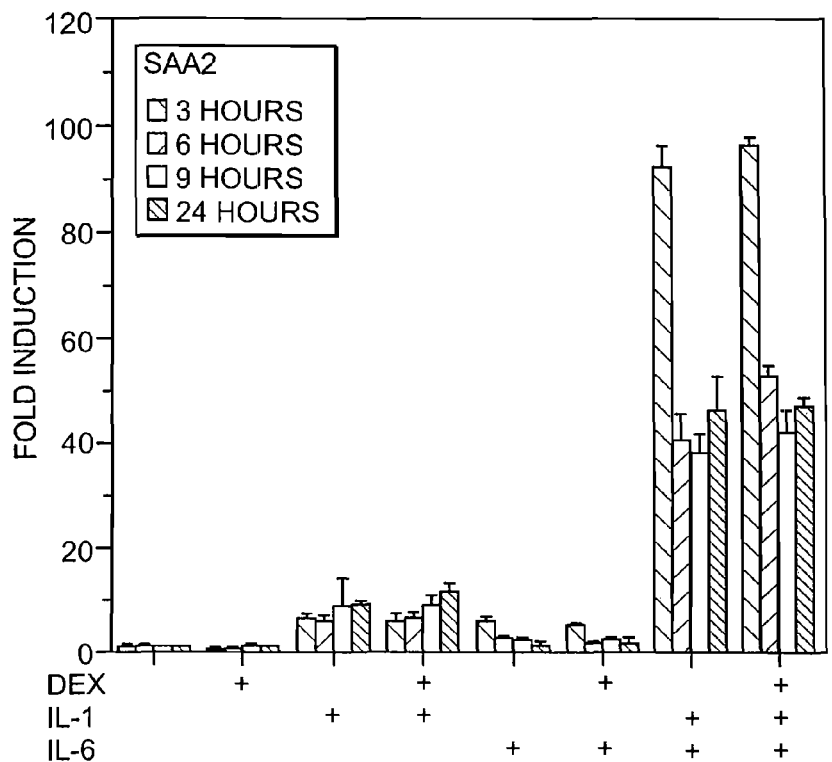
FIG. 2 is a timecourse of the induction of SAA1 and SAA2 promoter luciferase reporter constructs in the presence or absence of cytokine and/or dexamethasone treatment. HepG2 cells transfected with pGL2-SAA2pt (A) or pGL2-SAA1pt (B) luciferase reporter constructs were treated with medium only, dexamethasone (50 nM), IL-1 (10 ng/ml), IL-1 plus dexamethasone, IL-6 (10 ng/ml), IL-6 plus dexamethasone, IL-1 plus IL-6, or IL-1 plus IL-6 plus dexamethasone. Cells were harvested 3, 6, 9 and 24 hours after treatment and relative luciferase values were calculated and compared to untreated controls.

3'UTR that have no counterpart in the SAA1 3'UTR. (B) HepG2 cells were treated with medium only, 100 nM dexamethasone, 10 ng/ml IL-1 plus 10 ng/ml IL-6 or IL-1 plus IL-6 plus dexamethasone for 24 hours. RNA was extracted, reverse transcribed and amplified as described. PCR products were separated by 8% polyacrylamide gel electrophoresis. This image depicts the relative amounts of SAA1 and SAA2 product within each sample.

DETAILED DESCRIPTION OF THE INVENTION

The invention provides diagnostic assays for measuring the responsiveness of a subject, tissue, body fluid, or cell sample to a drug by comparing the mRNA levels of a gene that responds to the drug, such as a steroid, to the mRNA levels of a gene that does not respond to the drug. Methods according to the invention are useful to predict the ability of a subject (or a tissue, body fluid or cell sample in vitro) to respond to a drug or steroid before and at any stage of treatment, and to monitor the subject over time to assess continued responsiveness to the drug or steroid.

The preferred genes for measuring steroid responsiveness, for example, are serum amyloid A1 (SAA1), which is responsive to glucocorticoids both in vivo and in vitro, and serum amyloid A2 (SAA2), which is not responsive to glucocorticoids. The present inventors have used luciferase reporter constructs carrying the SAA1 and SAA2 promoters to demonstrate dose-dependent glucocorticoid enhancement of cytokine driven SAA1 transcription. The putative GRE in the SAA1 promoter was confirmed to be functional using reporter constructs carrying chimeric and mutant SAA promoters. SAA1 and SAA2 promoters exhibit qualitatively similar induction profiles in response to cytokines, but the SAA2 promoter had a significant basal and cytokine driven transcriptional advantage (i.e., between 2 and 3 fold) over the SAA1 promoter (see Example 1). The addition of the synthetic glucocorticoid dexamethasone to cytokine-treated cells specifically enhanced readout from the SAA1 promoter to a level that is similar to that of the SAA2 promoter. A combination of sequence alignment and in vitro experiments using reporter constructs carrying SAA1/SAA2 promoter chimeras and SAA1 and SAA2 promoters that had been modified by site specific mutagenesis identified a functional glucocorticoid response element (GRE) in the SAA1 promoter only.

An RT-PCR based method can be used to distinguish between the products generated by amplification from the SAA1 and SAA2 mRNAs (see Example 2 below). This method exploits differences in the 3'-untranslated regions (UTRs) of the transcripts, resulting in SAA1 mRNA being 26 residues shorter than SAA2 mRNA. Primers flanking the regions that contribute to this size disparity were used to amplify products of 335 and 361 base pairs (bp) from cDNA generated from the SAA1 and SAA2 mRNAs, respectively. The amplification products were resolved on 8% polyacrylamide gels and quantified by image analysis using NIH Image. Application of this method to total RNA extracted from HepG2 cells yielded results that parallel those obtained with the promoter reporter constructs. The ratio of SAA1 product to SAA2 product was 2:5 following treatment with IL-1 plus IL-6, indicating that the endogenous SAA2 gene has a significant transcriptional advantage (i.e., about 2.5 fold) when induced by cytokines in the absence of glucocorticoids. In contrast, the ratio of SAA1 to SAA2 product, from cells treated with IL-1 plus IL-6 plus dexamethasone was 5:4, indicating a "switch" in transcriptional advantage from SAA2 to SAA1 in the presence of steroids.

In the liver, upregulation of A-SAA protein synthesis during the acute phase response (APR) appears to be a two step process involving an initial cytokine driven phase followed by, or coincident with, a glucocorticoid enhanced cytokine dependent phase. During the first phase, in which the SAA1 and SAA2 promoters are engaged by the transcription factors NF-kappaB and NF-IL6, SAA2 has a significant transcriptional advantage over SAA1. In the second phase only the SAA1 promoter is additionally engaged by the GR, the result of which is to enhance its transcriptional activity to a level similar to that exhibited by the SAA2 promoter in both phases. In cells in which glucocorticoids can upregulate SAA1 transcription, but not SAA2 transcription, in the absence of cytokine stimulation, only the SAA1 promoter is engaged by the GR. Thus, the ratios of SAA1 and SAA2 RNAs and proteins may change over time with a bias strongly in favor of SAA2 in the early APR giving way to increasing relative amounts of SAA1 later. Furthermore, the absolute concentrations of each of the A-SAAs during chronic inflammation may depend on the nature of the underlying disease, and therefore the "mix" of pro- and anti-inflammatory mediators present. The introduction of anti-inflammatory steroid therapy may further modify the ratio of SAA1 and SAA2 mRNA depending on the type and therapeutic dose of synthetic glucocorticoids used.

Measurement of Gene Expression Levels

RNA Detection

In a preferred embodiment, gene expression is quantified at the RNA levels by amplification of the RNAs by, for example, reverse transcription polymerase chain reaction (RT-PCR) and resolution/quantification of the reaction products by gel electrophoresis (e.g., slab, capillary, etc.) and product measurement (e.g., by scanning, laser, etc.) or Northern blot analysis of the RNAs. Alternatively, RNA levels are quantified by in situ detection according to standard methods. In a preferred embodiment of the invention, probes capable of hybridizing specifically to SAA1 or SAA2 RNA, are attached to a solid phase support, e.g., a "chip," "DNA probe array" or "nucleic acid probe array". Oligonucleotides can be bound to a solid support by a variety of processes, including lithography. For example, a chip can hold up to about 250,000 oligonucleotides. The solid phase support is then contacted with a test nucleic acid and hybridization to the specific probes is detected. Accordingly, the quantification of numerous samples (e.g., different tissues from the same individual or samples from different individuals) or the profiling of the RNA levels of a number of steroid or drug responsive or non-responsive genes can be identified in a single hybridization experiment.

In another embodiment, an oligonucleotide ligation assay (OLA) (U.S. Pat. No. 4,998,617) may be used. The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides hybridize such that their termini abut, and create a ligation substrate. Ligation then permits the labeled oligonucleotide to be recovered using avidin, or another biotin ligand. Nickerson, D. A. et al. ((1990) *Proc. Natl. Acad. Sci. USA* 87:8923-27) have described a nucleic acid detection assay that combines attributes of PCR and OLA. In this method, PCR is used to achieve the exponential amplification of target DNA, which is then detected using OLA.

Several techniques based on this OLA method have been developed and are useful for detecting RNA. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996), *Nucleic Acids Res.* 24: 3728), OLA combined with PCR may permit the detection and quantification of SAA1 and SAA2 RNAs and other RNAs (e.g., CRP) in a single microtiter well. By marking each of the isoform-specific primers with a unique hapten, i.e., digoxigenin and fluorescein, each OLA reaction can be detected by using hapten specific antibodies that are labeled with different enzyme reporters, alkaline phosphatase or horseradish peroxidase. This system permits the detection of two closely related but distinct isoforms (e.g., SAA1 and SAA2 RNAs) using a high throughput format that leads to the production of two different colors. This system also permits the detection of additional RNAs, such as CRP.

Protein Detection

In another preferred embodiment, gene expression is quantified at the protein level using methods known in the art, for example using quantitative ELISA methods. Methods for designing and using quantitative ELISA assays are well known in the art. This method requires use of monoclonal or polyclonal antibodies that are specific for the closely related SAA1 and SAA2 proteins. Although the SAA1 and SAA2 proteins show substantial sequence identity, their amino acid sequences are sufficiently different to allow development of SAA1 and SAA2-specific anti bodies.

Suitable monoclonal antibodies may be prepared by standard hybridoma methods, using differential binding assays to ensure that the antibodies are specific for SAA1 and SAA2 and do not show cross-reactivity between the related proteins. Alternatively, suitable monoclonal antibodies may be prepared using antibody engineering methods such as phage display. Methods for obtaining highly specific antibodies from antibody phage display libraries are known in the art, and several phage antibody libraries are commercially available from, for example, MorphoSys (Martinsried, Germany), Cambridge Antibody Technology (Cambridge UK) and Dyax (Cambridge Mass.). Suitable phage display methods are described, for example, in U.S. Pat. Nos. 6,300,064 and 5,969,108, which are hereby incorporated by reference in their entirety. See also, for example "Antibody Engineering," McCafferty et al. (Eds.) (IRL Press 1996) and references therein.

In one method for, for example, preparing antibodies specific for SAA1, an antibody library displayed on filamentous bacteriophage is first adsorbed with SAA2 bound to a solid surface. The population of antibodies that does not bind to the surface-bound SAA2 is then panned over a SAA1 bound to a solid surface to identify antibodies that bind to SAA1. Antibody clones that bind to SAA1 then may be retested to show lack of binding to SAA2, as well as lack of cross-reactivity to other, non-related proteins. A similar approach may be used to prepare SAA2-specific antibodies. Phage display antibody methods can use libraries of antibodies in the Fab or scFv format. Once the antibody heavy and light chain genes are recovered from the phage antibodies, antibodies in any suitable format may be prepared, e.g. whole antibodies, Fab, scFv, etc.

Other antibody preparations may also be used, for example Camelid antibodies, which contain only heavy immunoglobulin chains. See, for example, Muyldermans et al. *J. Biotechnol.* June; 74(4):277-302 (2001) and references therein. Other antibody formats are described, for example in "Antibody Engineering," McCafferty et al. (Eds.) (IRL Press 1996).

Alternatively, polyclonal antibody preparations may be used for detection of steroid responsive gene products. Phage display methods also can be used to prepare reproducible populations of polyclonal antibodies. For example, an antibody library can be exhaustively-depleted of SAA2-binding clones by absorption on SAA2 bound to a solid surface, and then panned over a solid surface to identify antibodies that bind to SAA1. The resulting population of clones can also be depleted of cross-reactive clones by absorption over surfaces bearing irrelevant proteins, such as bovine serum albumin, etc., using methods well known in the art. This results in identification of a population of antibodies that specifically bind to SAA1, but not SAA2.

Polyclonal antibodies specific for SAA1 or SAA2 may also be prepared using traditional animal-based methods. Because of the sequence similarities between SAA1 and SAA2, it is likely that a large proportion of the antibody response against SAA1 administered to a rabbit, for example, would also bind to SAA2. The sequence comparison below shows that the amino acid differences between the C-terminal portion of SAA1 (SEQ ID NO:24) and the C-terminal portion of SAA2 (SEQ ID NO:25):

```
SAA1:  RSFFSFLGEA  FDGARDMWRA  YSDMREANYI  GSDKYFHARG
SAA2:  RSFFSFLGEA  FDGARDMWRA  YSDMREANYI  GSDKYFHARG

NYDAAKRGPG  GVWAAEAISD  ARENIQRFFG  HGAEDSLADQ

NYDAAKRGPG  GAWAAEVISN  ARENIQRLTG  HGAEDSLADQ

AANEWGRSGK  DPNHFRPAGL  PEKY

AANKWGRSGR  DPNHFRPAGL  PEKY
```

Accordingly, to reduce or eliminate this possibility, antipeptide polyclonal antibodies raised against short peptides derived from the C-terminal regions of SAA1 or SAA2 are used. Suitable peptides include, for example, AISD, IQRFF and AANE for SAA1, and VISN, IQRL and AANK for SAA2. These peptides can be conjugated at their N- or C-termini to carrier proteins such as bovine serum albumin (BSA) or keyhole limpet hemocyanin (KLH) and used to immunize animals, such as rabbits, using well-known immunization regimes. Specific polyclonal antibodies can be obtained from the serum of the animal by, for example, affinity chromatography over a matrix containing the peptide used for immunization bound to a solid support. Again, for example, antisera raised against SAA1 peptides can be adsorbed against SAA2 bound to a solid support to remove any cross-reactive antibodies, and vice-versa.

Methods for carrying out ELISA assays are well known in the art. Briefly, for example, a solid phase, such as an ELISA plate, is coated with a capture antibody that recognizes SAA and SAA2. After washing, antibodies specific for SAA1 and SAA2 are added. The specific antibodies may be applied to separate wells of the ELISA plate, and detected via their direct labeling (if appropriate), or by using secondary antibodies or secondary detection reagents (streptavidin-biotin) or labeled protein A or protein G. Alternatively, if the SAA1 and SAA2-specific antibodies are differentially labeled, detection can occur in the same sample, for example in the same well of the ELISA plate. This requires use of labels that produce distinct signals that can be independently quantified, for example by using dyes with different UV absorption maxima.

Other known protein detection methods may also be used in place of, or in addition to, ELISA assays. For example, when using antibodies against non-surface epitopes of the proteins, enzyme or chemical (e.g. CNBr) digestion of the proteins prior to detection may be used. For example, total SAA protein could be obtained using a generic antibody that binds to SAA1 and SAA2, followed by enzymatic protein digestion and detection with SAA1 and SAA2-specific antibodies. Improved methods for CNBr digestion of proteins are described in Kaiser et al, *Anal. Biochem. January* 1; 266(1): 1-8 (1999).

Other methods that can be used include Western Blot, immunohistochemistry, spot/slot blot techniques, and biosensors. For Western Blot, for example, duplicate proteins samples may be electrophoresed on an acrylamide gel and transferred to a membrane such as nitrocellulose or PVDF. One blot is detected with antibody for SAA1 and one blot is detected with antibody to SAA2. These primary antibodies are then detected, for example, with labeled secondary antibodies. Alternatively, antibodies specific for SAA1 and SAA2 are each labeled with a different fluorescent dye and are reacted with the same blot simultaneously. The fluorescence intensity of each dye is measured, and the ratio of the intensity indicates the ratio of the two proteins.

For immunohistochemistry, for example, duplicate tissue sections may be treated with antibodies specific to SAA1 and SAA2. These primary antibodies may be directly labeled or may be detected with suitable secondary antibodies. Staining intensity can be measured with a charge-coupled device (CCD) camera and the proteins quantitated. The ratio of the staining intensity indicates the ratio of the protein amounts. Alternatively, a single section can be stained with both antibodies if the antibodies have been labeled with different fluorescent labels.

Spot/slot blot techniques also are well known in the art. For example, identical amounts of protein samples may be directly spotted onto a membrane and detected with antibodies specific for SAA1 and SAA2 as described above.

Many types of biosensor-based methods are known in the art and may be used for detecting and quantitating SAA1 and SAA2. For example, antibodies specific to SAA1 or SAA2 may be bound to the surface of the biosensor such that when SAA1 or SAA2 binds to the coated surface a detectable change occurs in some property of the surface. Biosensors measure, for example, mass changes at the surface, some measure changes in electrical properties, and some measure changes in optical properties. Each of these methods are well known in the art and are suitable for use in the present methods.

Commercial biosensor-based methods are available from, for example, Biacore (Piscataway, N.J.) and are suitable for use in the present invention for detecting and quantitating changes in SAA1 and SAA2 expression. See also, for example, the protein detection methods described in U.S. Pat. No. 6,225,047, the contents of which are hereby incorporated by reference in their entirety, and Davies et al., *Biotechniques* 27(6):1258-61 (1999). Commercial protein chip detection methods are available from Ciphergen (Fremont, Calif.).

Mass spectrometric methods for protein detection may also be used to detect and quantify changes in SAA1 and SAA2 expression. See, for example, the methods described in U.S. Pat. Nos. 5,719,060, 5,894,063, and Shimizu et al., *J Chromatogr B Analyt Technol Biomed Life Sci* 25; 776(1):15-30 (2002); Kieman et al., *Anal Biochem* 301(1):49-56. (2002); and Pramanik et al., *Protein Sci* (11):2676-87 (2002). Mass spectrometry based protein detection methods are also available from Ciphergen (see supra).

Each of these detection methods may be used to detect and quantitate changes in expression of drug responsiveness markers in a manner analogous to that described above.

RNA and protein may be quantified from any tissue, body fluid or nucleated cell sample. In a preferred embodiment, the bodily fluid is blood that is obtained by known techniques (e.g., venipuncture). Alternatively, the methods according to the invention can be performed on dry cell samples (e.g., hair or skin) particularly when RT-PCR is used to amplify RNA. The tissue sample may be derived from a biopsy of any tissue in which the genes of interest (i.e., the drug or steroid responsive gene and the drug or steroid non-responsive gene) are expressed.

Preparations for oral administration of a drug or steroid may be suitably formulated to give controlled release of the active compound. For buccal administration, the drug or steroids may take the form of tablets or lozenges formulated in a conventional manner. Alternatively, an area may be swabbed, sprayed or applied with a steroid or drug prior to obtaining a post-treatment sample (e.g., by scraping). For administration by inhalation, the drug or steroid for use according to the methods of the invention is conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the drug or steroid and a suitable powder base such as lactose or starch.

The drugs or steroids may be formulated for parenteral administration by injection, e.g., by bolus injection or continuous infusion. Formulations for injection may be presented in unit dosage form, e.g., in ampoules or in multi-dose containers, with an added preservative. The drugs or steroids may take such forms as suspensions, solutions or emulsions in oily or aqueous vehicles, and may contain formulatory agents such as suspending, stabilizing and/or dispersing agents. Alternatively, the drugs or steroids may be in powder form for constitution with a suitable vehicle, e.g., sterile pyrogen-free water, before use.

The drugs or steroids may also be formulated in rectal drugs or steroids such as suppositories or retention enemas, e.g., containing conventional suppository bases such as cocoa butter or other glycerides.

The drugs or steroids may also be formulated as a depot preparation. For example, parenteral depot systems (PDS) are injected or implanted into the muscle or subcutaneous tissue and incorporated drug released in a controlled manner, allowing the adjustment of release rates over extended periods of time, ranging from several days up to one year. Such long acting formulations may be administered by implantation (e.g., subcutaneously or intramuscularly) or by intramuscular injection. The drugs or steroids may be formulated with suitable polymeric or hydrophobic materials (e.g., as an emulsion in an acceptable oil) or ion exchange resins, or as sparingly soluble derivatives, such as a sparingly soluble salt. Other suitable delivery systems include microspheres which offer the possibility of local noninvasive delivery of drugs over an extended period of time. This technology utilizes microspheres of precapillary size which can be injected via a coronary catheter into any selected part of the body, e.g., the eye, or other organs without causing inflammation or ischemia. The administered drug or steroid is slowly released from these microspheres and taken up by surrounding tissue cells.

Systemic administration of the drug or steroid can also be by transmucosal or transdermal means. For transmucosal or transdermal administration, penetrants appropriate to the barrier to be permeated are used in the formulation. Such penetrants are generally known in the art, and include, e.g., for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art. A wash solution may be used locally to treat an injury or inflammation to accelerate healing.

The invention also provides methods for determining the response of cells in vitro to exposure to a patient fluid sample. The differential steroid responsiveness of two or more inflammation-associated genes (e.g., the SAA1 and SAA2 genes and their promoters, by themselves, or together with the expression characteristics of other inflammation-associated genes such as CRP and their promoters) may be exploited to determine the relative capacity of a biological sample to induce the expression of inflammation-associated gene(s) (i.e., genes that are responsive to inflammation-related signals) in cultured primary and permanent cell lines. The biological sample under test may, for example, be: serum; plasma; cerebrospinal fluid; ascites fluid; synovial fluid; fluid harvested from a site of inflammation; fluid harvested from a pooled collection site; saliva; semen; bronchial lavage; and other types of samples collected from patients and healthy individuals. The biological sample under test may be added to tissue culture medium, a buffer, or used directly on cells.

Cultured primary or permanent cell lines may be: primary cells (including, but not restricted to, monocytes, synoviocytes, fibroblasts, endothelial cells) derived from the same subject as the fluid sample or derived from another individual; permanent cell lines from a range of tissue and organ origins (including, but not restricted to, cell lines available from public access repositories such as ATTC); or primary or permanent cell lines that have been stably transfected with "promoter-readout" constructs.

Readouts may be the ratios or absolute amounts of endogenous RNAs or proteins corresponding to the genes of interest including SAA1, SAA2 and other inflammation associated genes such as CRP. Readouts may also include constitutively expressed RNAs or proteins such as the glyceraldehyde phosphate dehydrogenase (GAPDH) gene. The ratios and absolute amounts of endogenous RNAs or proteins may be established using methods described above, such as the RT-PCR or ELISA methods and other quantitative and comparative methods described herein, or methods well known in the art, or equivalents thereof.

Readouts may also be derived from transiently or stably transfected DNA promoter-readout constructs carrying tandem or otherwise arranged promoter-reporter elements in which the promoters are SAA1 and/or SAA2 and/or CRP and/or promoters from other inflammation-associated genes and/or promoters from constitutively expressed genes such as GADPH. The reporters are sequences encoding molecules with distinct and distinguishable properties such as, but not limited to, firefly luciferase, renilla luciferase and green fluorescence protein. The readouts obtained may be proportional (i.e., ratios) to the reporter expression regulated by two or more promoters or may be absolute amounts of reporter gene expression. The arrangement of promoter-reporter elements within the same construct ensures that all of the elements that contribute to the composite proportional or absolute readout profile(s) are present in equimolar amounts.

The readouts (i.e., expression "profiles") will depend on the "mix" of inflammatory mediators and other signaling molecules present in the sample. It is expected that the profiles obtained from different samples will differ according to the presence and quantity of therapeutic agents that may alter the levels and/or the activities of inflammatory mediators and signaling molecules. Thus samples from healthy individuals, individuals with disease "A", individuals with disease "B", individuals undergoing partly successful therapy, and individuals undergoing fully successful therapy, etc., will all yield profiles that differ due to their inflammatory mediator and/or therapeutic agent mix. Thus, profiles may be specific for, or characteristic of, a particular disease, the severity of a particular disease, the stage of a particular disease, or the response to a given therapy in a particular disease.

In another embodiment, the methods of the invention are useful for monitoring the biological effect of a drug or combination of drugs in a patient. Cells are exposed to the patient's serum after they have been exposed to the drug(s). The cell may be any type of cell disclosed herein and may be, for example, a cell type which responds to the drug(s) by producing a signal (e.g., cellular proliferation or apoptosis) or a marker(s) (e.g., an mRNA or protein) that is indicative of the presence or activity of the drug. The marker may be the expression of endogenous SAA1, SAA2, CRP, and/or some other drug responsive gene. Alternatively, the marker may be the expression of an exogenous (i.e., transfected) gene which is driven by a promoter which is responsive to the drug (e.g., SAA1, SAA2, CRP or other drug responsive promoter).

Any promoter or endogenous gene which is an indicator of the effectiveness or activity of a drug may be used in the practice of the methods of the invention. For example, tacrolimus (Prograf) is a drug that inhibits T cell activation and is used to prevent rejection of transplanted organs. Tacrolimus inhibits an enzyme (calcineurin) crucial for the multiplication of T-cells. The methods of the invention may be used to measure responsiveness to drugs like tacrolimus by measuring the ability of serum from a patient being treated with that drug to stimulate T-cell activation (using a T cell line, for example) or by monitoring a protein or expression construct which is a marker for T-cell activation (e.g., is upregulated or downregulated in response to T cell activation), such as calcineurin or a reporter construct comprising the calcineurin promoter operatively linked to a reporter gene. Other drug activities that may be monitored with the methods of the invention include IL-1 receptor antagonists such as anakinra (Kineret); TNF-a antagonists such as infliximab (Remicade) and etanercept (Enbrel); antimetabolites such as methotrexate (Rheumatrex, Trexall) or 6-mercaptopurines such as azathioprine (Imuran); nonsteroidal anti-inflammatory drug (NSAIDs) such as the COX-2 inhibitors rofecoxib (Vioxx) and celecoxib (Celebrex); other immuno-suppressant drugs such as mycophenolate mofetil (Cellcept), Deoxyspergualin (DSG), sacrolimus (Rapamycin, Rapamune); and rheumatoid arthritis drugs such as leflunomide (Arava), for example.

The methods of the invention are useful therefore as a diagnostic and a prognostic tool, as a means for monitoring disease progression and resolution, for tracking the response, or lack thereof, to therapy, for evaluating the efficacy of alternative or concomitant medication; and for establishing the correct therapeutic dose of a medication. The methods of the invention may also be used, in the context of drug research and development, to assess the potential efficacy and side effects of investigational and approved drugs in biological samples collected in the course of animal testing and/or Phase I, II, III, and IV clinical trials and/or post-marketing studies.

The invention further provides for non-human transgenic animals, which are useful for a variety of purposes, e.g., studying steroid responsiveness in vivo in an animal model, identifying therapeutics for inflammatory diseases or toxicity testing. Transgenic animals of the invention include non-human animals containing a first reporter gene (e.g., green fluorescent protein) under the control of a drug or steroid responsive promoter and a second different reporter gene (e.g., yellow fluorescent protein) under the control of a drug and/or cytokine and/or steroid non-responsive promoter. In a preferred embodiment, a vector containing both reporter transgenes is used to make the transgenic animal. In a preferred embodiment, the human SAA1 and SAA2 gene promoters are used. In one embodiment, the reporter genes are the human SAA1 and SAA2 genes operatively linked to their own promoters, preferably on a single vector construct. Methods according to the invention are then practiced on the transgenic animals or their tissues, body fluids or cells. Such animals are useful for determining or monitoring drug or steroid responsiveness or dosing drugs or steroids in vivo, or studying the side effects of such drugs or steroids in an animal model. Such animals can also be used for studying drugs that are not primarily known to be anti-inflammatory or immune modifying, to establish whether they have an effect on inflammatory or immune processes (e.g., a side effect) for which the SAA1 and SAA2 transgenes provide a readout. An alternative embodiment would follow the above strategy using, for example, the human SAA1 and human CRP gene promoters or the human SAA2 and human CRP gene promoters.

Methods for obtaining transgenic non-human animals are well known in the art. For insertion, the SAA1 reporter and SAA2 reporter constructs are added to embryonic stem (ES) cells under appropriate conditions for the insertion method chosen, as is known to the skilled artisan. For example, if the ES cells are to be electroporated, the ES cells and constructs are exposed to an electric pulse using an electroporation machine following the manufacturer's guidelines for use. After electroporation, the ES cells are typically allowed to recover under suitable incubation conditions. The cells are then screened for the presence of the SAA1 and SAA2 construct(s). Where more than one construct is to be introduced into the ES cell, each construct can be introduced simultaneously or one at a time. In a preferred embodiment, a single construct having both the SAA1 reporter and the SAA2 reporter (SAA1/SAA2 construct) is used.

After suitable ES cells containing the SAA1/SAA2 construct in the proper location have been identified, the cells can be inserted into an embryo. Insertion may be accomplished in a variety of ways known to the skilled artisan, however a preferred method is by microinjection. For microinjection, about 10-30 cells are collected into a micropipet and injected into embryos that are at the proper stage of development to permit integration of the foreign ES cell containing the SAA1/SAA2 construct into the developing embryo. For instance, the transformed ES cells can be microinjected into blastocytes. The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan.

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the SAA1/SAA2 construct by looking for mosaic coat color (indicating that the ES cell was incorporated into the developing embryo). Thus, for example, if the ES cell line carries the genes for white fur, the embryo selected carries the genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2-3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the SAA1/SAA2 construct using Southern blots and/or PCR as described above. Offspring that appear to be mosaics may then be crossed to each other, if they are believed to carry the SAA1/SAA2 construct in their germ line, in order to generate homozygous transgenic animals. Homozygotes may be identified by Southern blotting of equivalent amounts of genomic DNA from mice that are the product of this cross, as well as mice that are known heterozygotes and wild type mice.

Other means of identifying and characterizing the SAA1/SAA2 offspring are available. For example, Northern blots are useful for probing the mRNA for the presence or absence of transcripts encoding one or both of the marker genes. In addition, Western blots are useful to assess the level of expression of the marker gene in various tissues of the offspring by probing the Western blot with an antibody against one or both marker proteins, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the SAA1/SAA2 construct gene product.

EXAMPLES

Example 1

Differential SAA1 and SAA2 Promoter Engagement in a Series of Unmodified and Modified Promoter Reporter Constructs Transfected into Human HepG2 Hepatoma Cells Using Various Combinations of IL-1, IL-6 and Glucocorticoids SAA Promoter Luciferase Reporter Constructs The pGL2-SAA2pt construct, which contains 1.2 kb of the human SAA2 promoter upstream of a luciferase reporter was generated as follows. A 1196 bp of the promoter region and 22 bp of the first exon of the human acute phase SAA2 gene was amplified by PCR with the introduction of MluI and XhoI restriction sites at the 5' and 3' ends respectively (5' oligonucleotide: 5' AAGAATTCACGCGTCCATGCATGT-TGCGGCCGCTTGGCCATCCTT-TACTTCCT-'3' (SEQ ID NO: 8); 3' oligonucleotide: 5'-TTGAATTCCTCGAGCAG-GTA-CCATACATATGTAGCTGAGCTGCGGGTCC-3' (SEQ ID NO:9). The PCR product was subsequently cloned into the multiple-cloning site of the pGL2-Basic vector (Promega, Madison, Wis., USA) which is located upstream of a luciferase reporter gene.

The pGL2-SAA1pt construct was generated as follows. The proximal 3.1 kb of genomic sequence upstream of the human SAA1 transcription start site plus the full 37 bases of 5'UTR was amplified by polymerase chain reaction (PCR) from human genomic DNA (Roche Biomolecular) using forward and reverse primers, HSAA1PF (5'-GAAT-TCACGCGTTT-GGGCAGGGAATATACTTATTTATG-GAAG-3') (SEQ ID NO:10) and HSAAPR (5'-GAATTCCCATGGTGCTGATCTGTGCTGTA-GCTGAGCTGCGGG-3') (SEQ ID NO:11), that incorporate Mlu1 and Nco1 restriction sites, respectively. The product was digested with Mlu1 and Nco1 and directionally cloned into a pGL2 vector which had been modified to include an Nco1 site at the start of the luciferase coding sequence and contains the human SAA2 3'UTR (Longley et al. (1999) J. Immunol. 163:4537-45).

Constructs pGL2-SAA1[0.7] and pGL2-SAA1[0.25] containing 704 and 233 bases of promoter sequence respectively, were generated from pGL2-SAA1pt by PCR using the forward primers 5'-GAATTCACGCGTGCGTGATTATAGCT-CACTG-CAGCCTTGACC-3' (SEQ ID NO:12) and 5'-GAATTCACGCGTGGTCT-CCTGCCTG-3' (SEQ ID NO:13) respectively, and the reverse primer HSAAPR.

Constructs pGL2-SAA2[0.7] and pGL2-SAA2[0.25] containing 700 and 239 bases of promoter sequence respectively, were generated from pGL2-SAA2pt by PCR using the forward primers 5'-TATAACGCGTCCTATTTAACGCACCA-CACTCT-3' (SEQ ID NO:14) and 5'-GAATTCACGCGT-GATCTAGCACCTG-3' (SEQ ID NO:15) respectively, and the reverse primer HSAAPR.

Chimeric promoter constructs containing combinations of defined regions of the SAA1 and SAA2 promoters were generated by restriction digest of pGL2-SAA1[0.7] and pGL2-SAA2[0.7] with Xma1 and heterologous ligation of each linearized distal promoter region with the reciprocal linearized proximal promoter region and vector sequence. The chimeric SAA1/2 promoter contains bases −704 to −164 of SAA1 and −159 to −1 of SAA2. The reciprocal SAA2/1 promoter chimera contains bases −700 to −160 of SAA2 and −163 to −1 of SAA1. The control chimera SAA1/1 was generated by re-ligation of bases −704 to −164 of SAA1 and −163 to −1 of SAA1. The control chimera SAA2/2 was generated by re-ligation of bases −700 to −160 of SAA2 and −159 to −1 of SAA2.

The GREI construct was generated by PCR mutagenesis of pGL2-SAA1[0.7] using primers GREIF (5'-CAGCAAAC-CTCTCTTGTCCC-3') (SEQ ID NO:16) and GREIR (5'-AGAGAGGTTTGCTGTGCCT-3') (SEQ ID NO:17). The GRED construct was generated by PCR mutagenesis of pGL2-SAA2[0.7] using primers GREDF (5'-CAAGGCA-CATCTTGTTC-CCATAGGT-3') (SEQ ID NO:18) and GREDR (5'-GGAACAAGATGTGCCTTGGCAATG-3') (SEQ ID NO:19). The integrity of all constructs was verified by DNA sequencing.

The renilla transfection control plasmid is described elsewhere (Behre et al. (1999) Biotechniques 26:24-6, 28). The constitutive human Glucocorticoid Receptor-α expression plasmid, CMX-GR, was obtained from Dr. Ron Evans, The Salk Institute, La Jolla, Calif. (Doucas et al. (2000) Proc. Natl. Acad. Sci. USA 97:11893-8).

Cell Culture and Transient Transfection

Human HepG2 hepatoma cells (ATCC) were cultured in DMEM containing 10% FCS, gentamycin, sodium pyruvate and non-essential amino acids (Gibco BRL). Cells were seeded into 24 well plates 24 hours prior to transfection using FuGENE (Roche Biomolecular) as described in Jensen et al. (2000) J. Immunol. 164:5277-86. Cells transfected with SAA promoter luciferase reporter constructs and renilla control plasmid, were incubated for 16 to 20 hours before replacement of culture medium with fresh medium alone or fresh medium containing 10 ng/ml cytokines and/or dexamethasone and/or RU486 (Mifepristone). IL-1 was purchased from Peprotech. IL-6 was obtained from AstraZeneca. Dexamethasone and RU486 were obtained from Sigma.

Luciferase Assays

Cells were harvested at various times post-treatment, washed in PBS and resuspended in Passive Lysis Buffer (Promega, Madison, Wis.). Lysates were assayed for luciferase and renilla activity using the LLR and Stop and Glo reagents (Promega) in a dual injection luminometer (Turner Designs, Sunnyvale, Calif.). Each treatment was carried out in triplicate and the mean ratio of luciferase to renilla activity and standard deviations were calculated. The ratios are expressed relative to untreated controls and are representative of three independent experiments.

RT-PCR

Total RNA was prepared by LiCl Urea extraction (Auffray and Rougeon (1980) Eur. J. Biochem. 107:303-14) from HepG2 cells treated for 24 hours under various experimental conditions. RT-PCR was carried out in a two step process. cDNA was reverse transcribed from 3 μg of total cellular RNA in a 25 μl reaction containing oligo dT primer, Rnasin, RNase inhibitor and Moloney Murine Leukemia Virus Reverse Transcriptase (Promega) at 42° C. for 1 hour. PCR was performed using 2 μl of cDNA product in a 50 μl reaction containing 125 μM primers, 200 μM dNTPs (Pharmacia Amersham, Piscataway, N.J.), 1×PCR buffer, 5 mM $MgCl_2$, and AmpliTaq polymerase (Perkin Elmer-Roche, Indianapolis, Ind.). The forward primer was 5'-CAGACAAATACTTC-CATGCT-3' (SEQ ID NO:20); the reverse primer was an equal mix of 5'-TTTTTTCCACCTCTTAAGTATT-TATTAGA-3' (SEQ ID NO:21) and 5'-TTTTTTCCA-CCTCTTAAGCATTTATTAGA-3' (SEQ ID NO:22). PCR conditions were as follows: 95° C. for 5 minutes, followed by 25 cycles of 94° C. for 20 seconds, 51° C. for 1 minute, 72° C. for 1 minute, followed by 72° C. for 5 minutes. Products were separated on 8% polyacrylamide gels at 50 v for 24 hours, stained with ethidium bromide and quantified by NIH Image.

Computer Analysis

Transcription factor consensus binding site predictions were made using the Signalscan and TESS programs available from the Center for Bioinformatics at the University of Pennsylvania at www<dot>cbil<dot>upenn<dot>edu. Sequence alignments were carried out using the ClustalW program (Thompson et al. (1994) Nucleic Acids Res. 22:4673-4680) available at pbil<dot>ibcp<dot>fr/cgibin/npsa_automat<dot>pl?page=/NPSA/npsa_clustalwan<dot>html.

Sequence Alignment of the Proximal Promoters of SAA1 and SAA2

Alignment of 0.7 kB of the SAA1 and SAA2 sequences immediately upstream of their respective transcription start sites, using the ClustalW program, revealed a very high degree of sequence identity (87%) in the proximal ~450 bp, upstream of which the sequences exhibit a markedly decreased level of identity and many regions of non-contiguity. The alignment of the highly conserved proximal promoter regions is depicted in FIG. 1. Within this alignment there are two short non-contiguous regions that each mandate the introduction of a gap of more than one residue into one of the promoter sequences. These "deletions" are in SAA1 relative to positions −207 to −199 in SAA2 and in SAA2 relative to positions −43 to −40 of SAA1. Close visual inspection revealed a putative 15 base pair GRE consensus sequence (GGCACATCTTGTTCC) (SEQ ID NO:23) (Scheidereit et al. (1983) Nature 304:749-52) in SAA1 (from −208 to −194 of SEQ ID NO:1) that encompasses the first of these non-contiguous regions. These residues are also present in SAA2 (within the sequence from −213 and −190 of SEQ ID NO:2) but are disrupted" by 9 residues from −207 to −199 that have no counterparts in the corresponding location in SAA1 (i.e., between SAA1 residues −203 and −202).

Figure 2B:
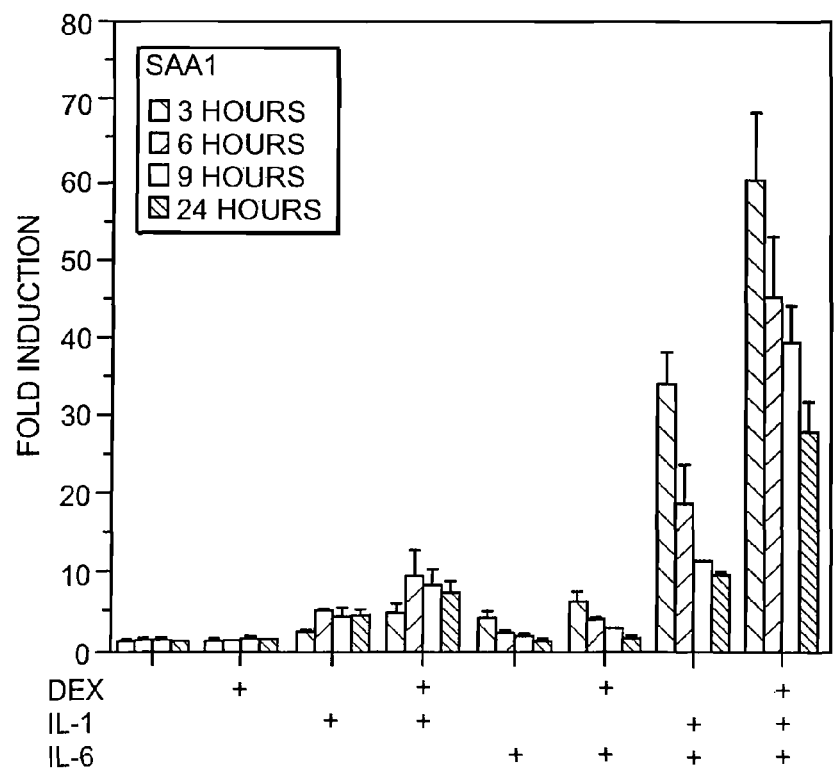

Transcriptional Regulation of the SAA1 and SAA2 Promoters In Vitro by Cytokines and Glucocorticoids To establish the extent to which the SAA1 and SAA2 promoters exhibit qualitatively and quantitatively similar responses to cytokines, and to determine whether the putative SAA1 GRE defined above is functionally active, various reporter constructs containing native and modified SAA1 and SAA2 promoters were assayed for their responsiveness to cytokines and glucocorticoids in vitro. HepG2 cells transfected with either of the A-SAA promoter luciferase reporter constructs, pGL2-SAA1pt or pGL2-SAA2pt, were treated with cytokines for 3, 6, 9 and 24 hours. The SAA2 promoter was moderately induced by IL-1 alone or IL-6 alone and synergistically induced by the simultaneous addition of both cytokines (FIG. 2A). IL-1 driven readout increased from 3 to 24 hours, whereas IL-6 driven readout was highest at 3 hours and decreased through 24 hours. The synergistic response to dual treatment with IL-1 plus IL-6 followed a kinetic profile similar to that observed for IL-6 alone. These results were all in accord with data previously reported by us (Uhlar et al. (1997) J. Immunol. Meth. 203:123-30). The SAA1 promoter exhibited transcription induction profiles in response to single and dual cytokine treatments that were qualitatively and kinetically similar to those of the SAA2 promoter (FIG. 2B). However, SAA2 appeared to have a considerable (~2-3 fold) quantitative transcriptional advantage over SAA1 in response to all three cytokine treatments. Treatment of transfected cells with dexamethasone alone had no effect on the SAA1 promoter. However, co-treatment of transfected cells with 50 nM dexamethasone enhanced the cytokine driven induction of the SAA1 promoter approximately two-fold for all treatments at all timepoints (FIG. 2B). In contrast, dexamethasone had no measurable effect on SAA2 promoter activity under any of the assay conditions (FIG. 2A). These data establish that the SAA1 and SAA2 genes respond differentially to glucocorticoids in the context of an ongoing cytokine dependent transcriptional induction.

A construct containing only 235 bases of the SAA1 promoter (pGL2-SAA1[0.25]) retained all of the quantitative, qualitative and kinetic aspects of cytokine responsiveness and glucocorticoid enhancement exhibited by constructs containing 3.1 kb of sequence upstream of the SAA1 transcription start site, suggesting that all of the critical control elements engaged by the most important inflammatory mediators are located in this short region (data not shown).

Figure 3:
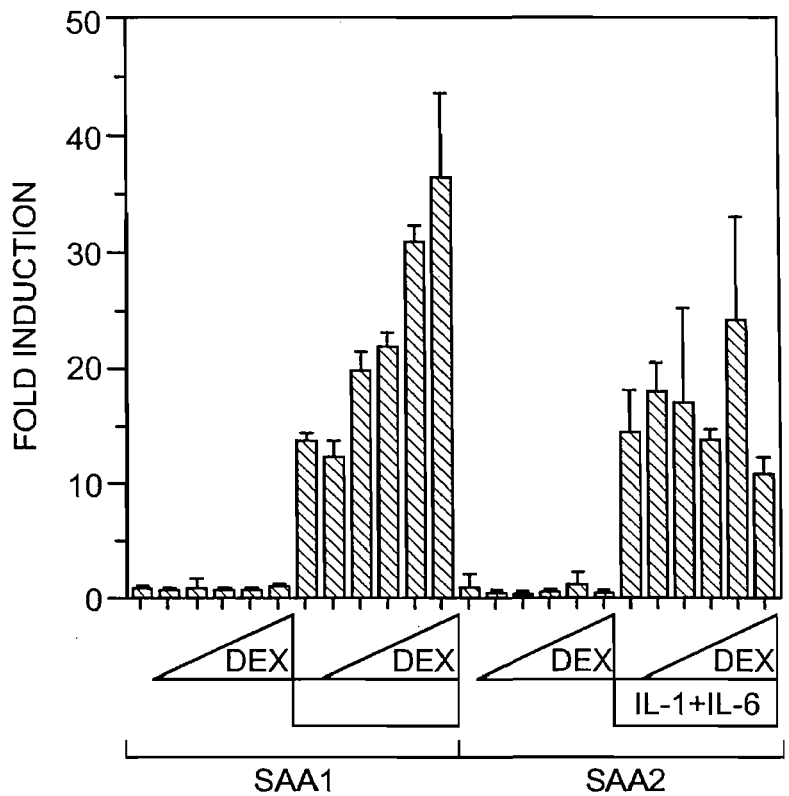
FIG. 3 shows that SAA1 glucocorticoid responsiveness is dose dependent. HepG2 cells transfected with pGL2-SAA1pt or pGL2-SAA2pt were treated with increasing amounts of dexamethasone (10 nM, 50 nM, 100 nM, 500 nM, 1 µM) in the absence or presence of 10 ng/ml IL-1 plus 10 ng/ml IL-6. Cells were harvested 4 hours after treatment and relative luciferase values were calculated and compared to untreated controls.

Dose Dependent Glucocorticoid Enhancement of Cytokine Driven SAA1 Promoter Activity To determine whether the non-responsiveness of the SAA1 and SAA2 promoters to dexamethasone alone and of the SAA2 promoter to dexamethasone in the context of cytokine induction was due to sub-optimal dosing, a range of dexamethasone concentrations was assayed. HepG2 cells transfected with either pGL2-SAA1pt or pGL2-SAA2pt were treated with 10 nM, 50 nM, 100 nM, 500 nM or 1 μM dexamethasone in the presence or absence of IL-1 plus IL-6 for 4 hours (FIG. 3). Neither promoter showed any response to dexamethasone alone, even at the highest dose used. In contrast to the cytokine driven transcriptional readout from the SAA2 promoter, which could not be enhanced by dexamethasone at any concentration, the SAA1 promoter exhibited a clear dose dependent enhancement of transcriptional activity. This suggests that the dexamethasone enhancement of cytokine driven SAA1 promoter activity involves specific receptor mediated events, most likely via glucocorticoid receptors (GRs).

The Enhancement of Cytokine Driven SAA1 Promoter Transcriptional Activity by Glucocorticoids is Glucocorticoid Receptor (GR) Dependent.

Figure 4:
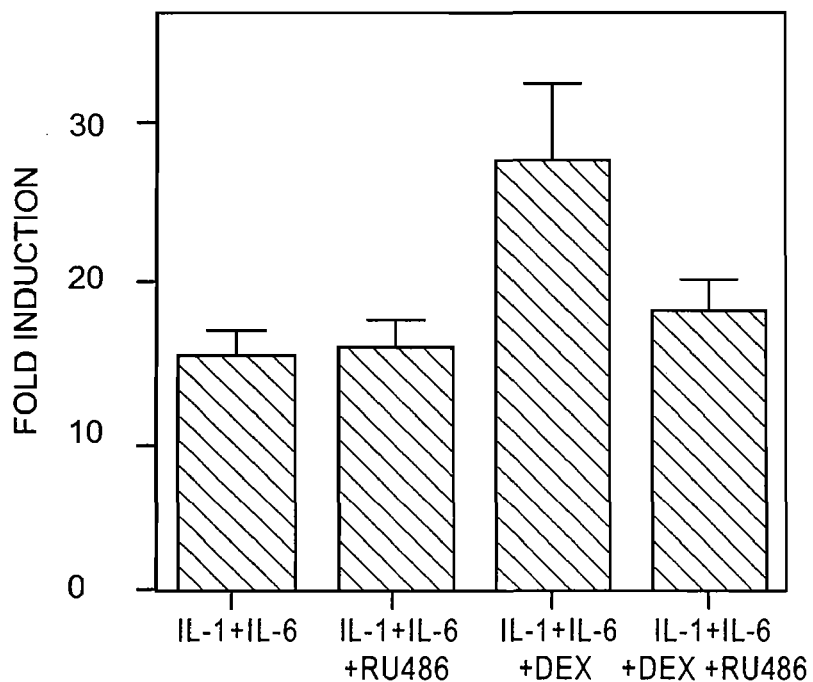
FIG. 4 shows that SAA1 glucocorticoid responsiveness is glucocorticoid receptor (GR) dependent. HepG2 cells were transfected with pGL2-SAA1pt and treated with 10 ng/ml IL-1 plus 10 ng/ml IL-6, alone and in the presence of 10 nM RU486 and/or 100 nM dexamethasone. Cells were harvested 4 hours after treatment and relative luciferase values were calculated and compared to untreated controls.

To establish that the enhancement of cytokine dependent SAA1 promoter transcriptional activity by glucocorticoids is mediated by the GR, cytokine and dexamethasone treatments similar to those described above were carried out in the presence of the GR antagonist RU486 (Mifepristone). HepG2 cells transfected with pGL2-SAA1pt were treated with IL-1 plus IL-6, in the presence or absence of 100 nM dexamethasone and/or 10 nM RU486 for 4 hours (FIG. 4). The presence of RU486 alone had no measurable effect on the level of cytokine driven SAA1 promoter transcriptional activity. However, RU486 completely blocked the capacity of dexamethasone to quantitatively enhance the induction of the SAA1 promoter by cytokines, limiting the transcriptional readout to that observed in transfected cells treated only with cytokines. This established that the GR is a requisite component in mediating the dexamethasone enhancement of cytokine driven SAA1 transcriptional activity.

The Effect of GR Over-Expression on the Capacity of Dexamethasone to Modify SAA1 and SAA2 Gene Transcriptional Activity HepG2 cells have been reported to express only low levels of GR (Baumann et al. (1990) J. Biol. Chem. 265:22275-81). To determine whether the non-response of both promoters to dexamethasone alone, and that of the SAA2 promoter to dexamethasone in the context of cytokine induction, is due to cellular GR levels that are below a functional threshold, SAA1 and SAA2 transcriptional readout was measured in HepG2 cells co-transfected with a constitutive GR expression construct after treatment with various combinations of cytokines and dexamethasone (FIG. 5).

Figure 5A:
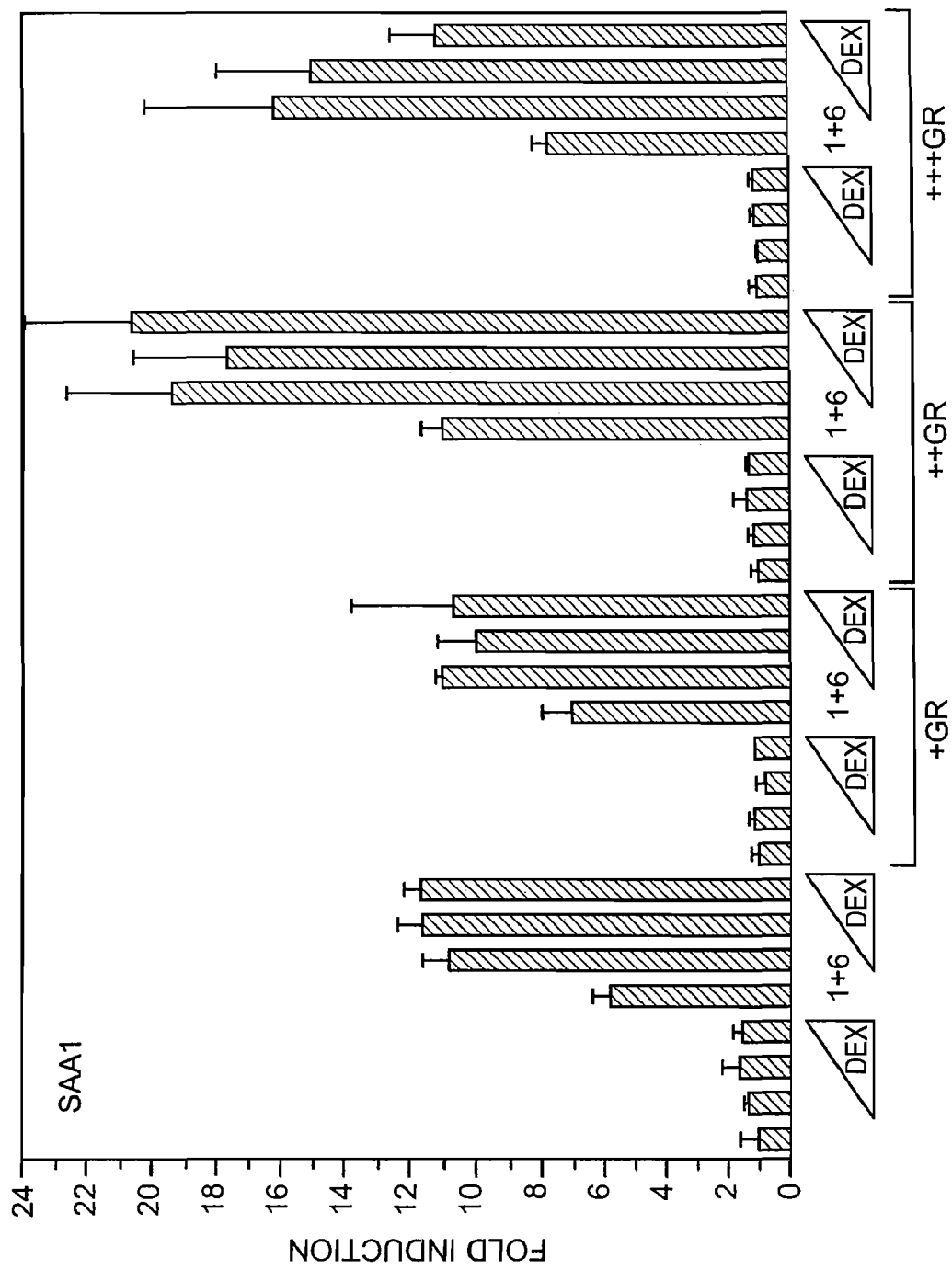
FIG. 5 shows that SAA1 glucocorticoid responsiveness is dependent on cytokine driven transcriptional activation. HepG2 cells co-transfected with the pGL2-SAA1[0.25] (A) or pGL2-SAA2[0.25] (B) and 0, 5, 25 or 50 ng/well CMX-GR expression construct were treated with increasing amounts of dexamethasone (0, 50 nM, 500 nM, 5 µM) in the absence or presence of 10 ng/ml IL-1 plus 10 ng/ml IL-6. Cells were harvested 4 hours after treatment and relative luciferase values were calculated and compared to untreated controls.
Figure 5B:
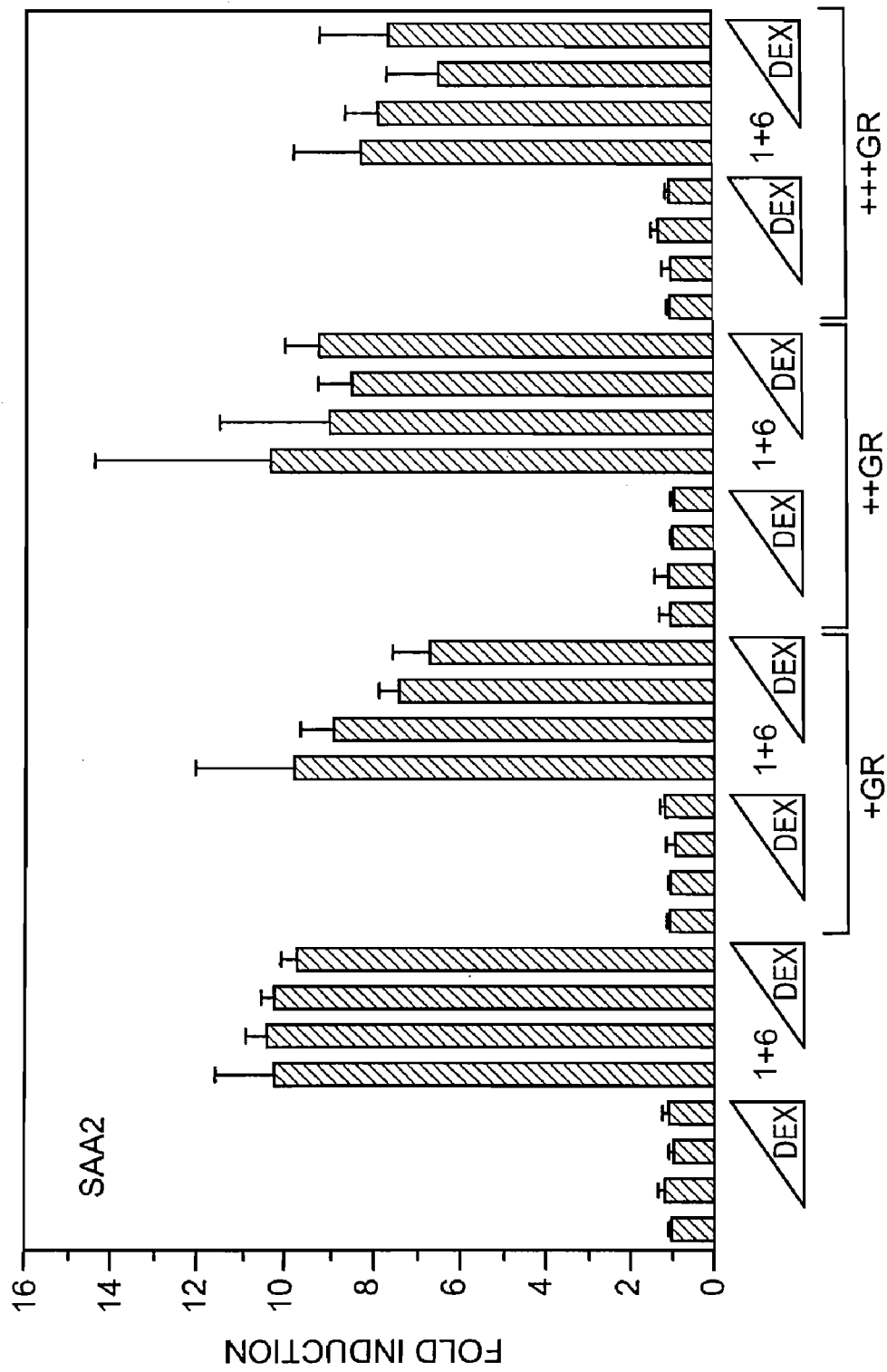

The SAA1 and SAA2 promoters remained non-responsive to dexamethasone alone in HepG2 cells co-transfected with 5, 25 or 50 ng/well of GR expression construct together with pGL2-SAA1pt or pGL2-SAA2pt. However, in the context of cytokine induction of the SAA1 promoter, the dexamethasone enhancement of cytokine driven transcriptional readout could be augmented by co-transfection with the higher amounts (i.e., 25 or 50 ng/well) of GR expression construct (FIG. 5A). These results suggest that the glucocorticoid signaling capacity of native HepG2 cells is not maximized with respect to engagement of the SAA1 promoter GRE. In contrast, co-transfection of GR expression vector could not bring about a dexamethasone dependent enhancement of cytokine driven transcriptional readout from the SAA2 promoter even when cells transfected with the highest levels of GR construct were treated with the highest concentrations of dexamethasone (FIG. 5B). The latter results establish that the SAA2 promoter is truly non-responsive to glucocorticoids.

Chimeric Promoters Containing the Putative SAA1 GRE Retain Glucocorticoid Responsiveness The SAA1 and SAA2 proximal promoter regions each contain XmaI restriction enzyme sites that are similarly positioned in a highly conserved region immediately downstream of the NF-IL6 site, which itself is immediately downstream of the "GRE" region (FIG. 1). The XmaI site was used to generate chimeras in which the SAA1 and SAA2 "GRE" regions could be reciprocally ligated to the SAA1 and SAA2 proximal promoter regions spanning the approximately 160 bp adjacent to the transcription start site of each gene. The proximal promoter regions are highly conserved (93% identical) and each contain the critically important NfkappaB site in addition to a putative site (between −110 and −102 of SAA1 and −106 and −98 of SAA2) for the transcriptional repressor YY-1; the major difference is a "deletion" in the SAA2 promoter of four residues that are present in the SAA1 promoter between residues −44 and −39 (FIG. 1). The experiments outlined above established that all of the major cytokine and glucocorticoid response elements, together with the promoter feature that confers an apparent baseline and cytokine responsive transcriptional advantage to the SAA2 gene are located within 250 bases of the transcription start site. The chimeric constructs were used to determine the locations of the elements that mandate qualitative and quantitative transcriptional differences between the SAA1 and SAA2 genes relative to the XmaI site.

Figure 6:
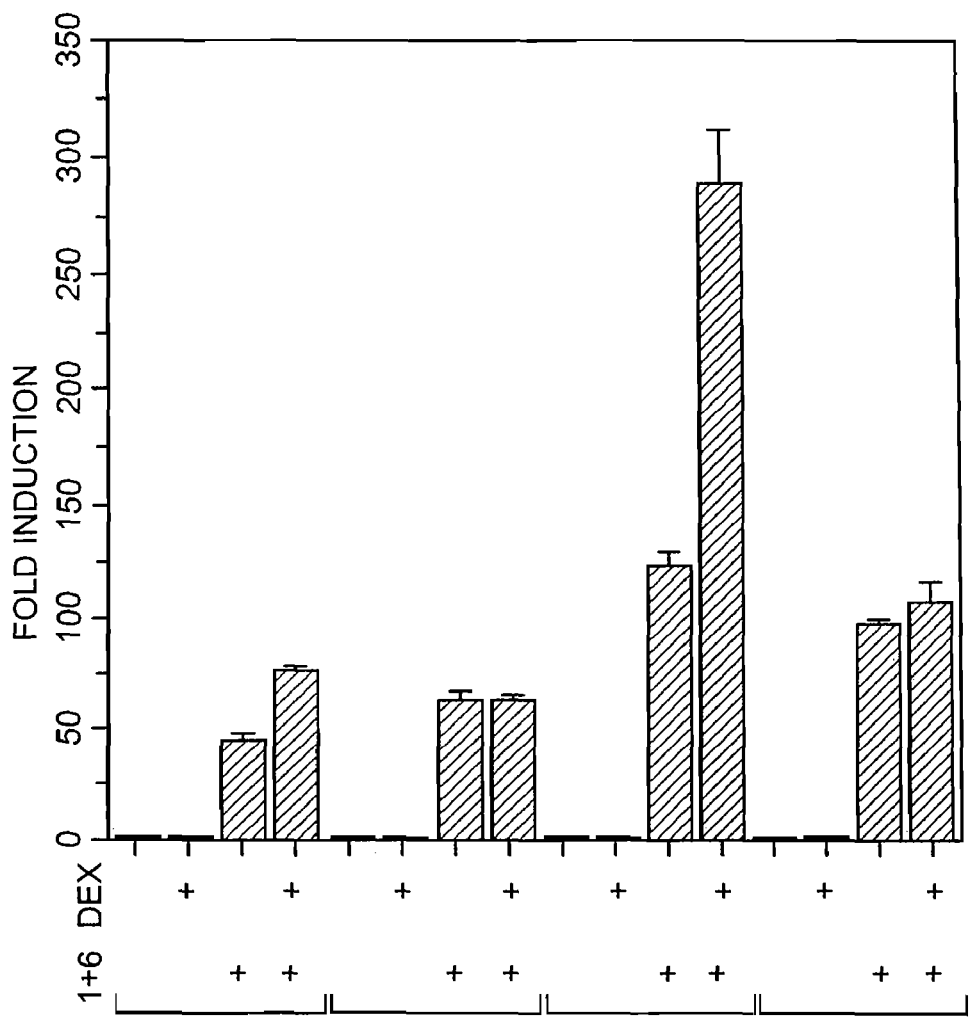
FIG. 6 shows cytokine and dexamethasone induction of chimeric SAA promoters. In the schematic diagram of the chimeric SAA promoter constructs, the sequence derived from SAA1 is represented by pale gray shading; sequence derived from SAA2 is represented by dark gray shading; the luciferase coding sequence is represented by "Luc"; the transcription start site is indicated with an arrow. The positions of the Xma1 restriction enzyme sites used for generating the chimeras are indicated. The putative GRE is represented by a black box. Chimeric constructs were transfected into HepG2 cells and treated with medium only, 50 nM dexamethasone, 10 ng/ml IL-1 plus 10 ng/ml IL-6, or IL-1 plus IL-6 plus dexamethasone. Cells were harvested 4 hours after treatment and relative luciferase values were calculated and compared to untreated controls.

Constructs SAA1/1 and SAA2/1, each of which contain the proximal 163 bp of the SAA1 promoter region, exhibited basal and cytokine driven levels of transcriptional activity that are characteristic of the unmodified SAA1 promoter (FIG. 6). Similarly, constructs SAA1/2 and SAA2/2, each of which contain the proximal 159 bp of the SAA2 promoter region, had basal and cytokine driven levels of transcriptional activity that are characteristic of the unmodified SAA2 promoter. Taken together, these experiments suggest that quantitative differences in both the basal and cytokine-driven transcriptional regulation of the SAA1 and SAA2 genes are mandated by minor sequence differences between the respective promoters in the region downstream of the XmaI site. Constructs SAA1/1 and SAA1/2, which contain the distal region of the SAA1 promoter (i.e., upstream of the XmaI site) including the putative GRE, were each responsive to dexamethasone in the presence of cytokines. Constructs SAA2/1 and SAA2/2 contain the distal region of the SAA2 promoter and were each non-responsive to dexamethasone. These data strongly suggest that a genetic element in the region between bases −704 and −164 of the SAA1 promoter, most likely the sequence between −208 and −194 that conforms to the GRE consensus, confers the property of glucocorticoid modifiable transcriptional activity to the SAA1 gene.

Confirmation that the Putative GRE in SAA1 is Functional

Figure 7B:
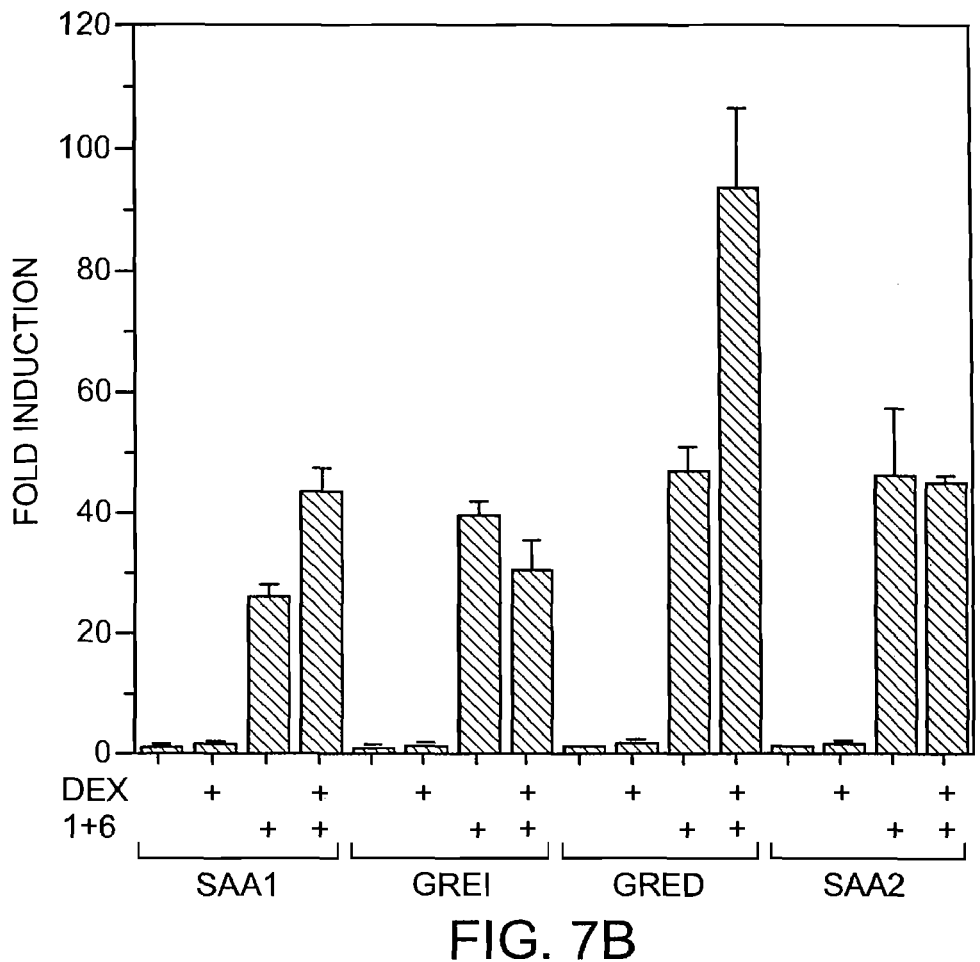
FIG. 7 shows GRE mutant SAA promoters. (A) Alignment of the region of SAA1 encompassing the GRE (SEQ ID NO:26), the corresponding regions of SAA2 (SEQ ID NO:29), the mutants GREI (SEQ ID NO:27) and GRED (SEQ ID NO:28) and the consensus GRE sequence (SEQ ID NO:1). (B) HepG2 cells were transfected with pGL2-SAA1 [0.7], GRET, GRED or pGL2-SAA2[0.7] constructs and treated with medium only, 50 nM dexamethasone, 10 ng/ml IL-1 plus 10 ng/ml IL-6, or IL-1 plus IL-6 plus dexamethasone. Cells were harvested 4 hours after treatment and relative luciferase values were calculated and compared to untreated controls.

Site directed mutagenesis experiments were performed to determine whether the putative SAA1 GRE is functional and to exclude the possibility that subtle differences in genomic context, rather than intrinsic sequence differences in the putative SAA1 GRE and SAA2 "disrupted GRE", mandate the differential dexamethasone responsiveness of the genes (and chimeric derivatives thereof). Two modified constructs were generated: the GREI construct contains an SAA1 promoter with a 9 residue sequence (GCAAACCTC) (Nucleotides −207 to −199 of SEQ ID NO:2) inserted into the GRE to form an "SAA2-like disrupted GRE"; the GRED construct contains an SAA2 promoter in which the same 9 residues have been deleted to form an "SAA1-like GRE" (FIG. 7A). The GREI and GRED constructs each retained the basal and cytokine driven levels of transcriptional activity that are characteristic of the unmodified parental promoters from which they were derived. However, the GREI construct had "lost" the capacity to respond to dexamethasone in the presence of cytokines, whereas the GRED construct had "gained" this property (FIG. 7B), thereby establishing that the SAA1 GRE is functional and is both necessary and sufficient to confer glucocorticoid responsiveness in the context of cytokine stimulation.

Example 2

Use of the RT-PCR Assay to Establish that the Ratio of SAA1 and SAA2 Products in HepG2 Cells Treated with IL-1 Plus IL-6 Changes According to Whether Glucocorticoid is Present, in a Manner Analogous to that Defined in Promoter-Reporter Studies To determine whether the results obtained using the SAA1 and SAA2 promoter luciferase reporter constructs accurately reflect the regulation of the endogenous genes with respect to cytokines and glucocorticoids, an RT-PCR method was developed whereby the relative proportions of the transcription products of each gene could be directly compared. The SAA1 and SAA2 mRNAs, although highly similar (91% identical overall), differ significantly in the central region of their 3'UTRs; the SAA1 mRNA 3'UTR relative to that of the SAA2 mRNA 3'UTR has four "deletions" totaling 26 residues (FIG. 8A).

Forward and reverse PCR primers were designed, each of which can bind cDNA derived from either A-SAA mRNA (FIG. 8A). RT-PCR using these primers generates bands of 335 and 361 base pairs corresponding to products generated from the SAA1 and SAA2 mRNAs respectively. In addition, the primers span intron 3 of each gene, thereby permitting products of amplification from contaminating genomic DNA to be identified. The ratio of 335 bp to 361 bp products, as determined by image analysis following resolution on 8% polyacrylamide gels reflects the relative concentrations of cellular SAA1 and SAA2 mRNAs and serves as a surrogate measure or readout of the transcriptional activation of the SAA1 and SAA2 promoters.

Figure 8B:
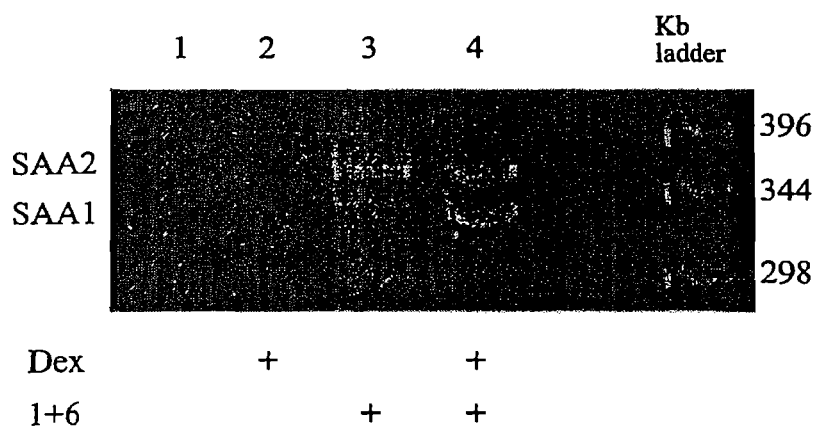
FIG. 8 shows the response of the endogenous human SAA1 and SAA2 genes to cytokines and dexamethasone. (A) Alignment of the 335 bp SAA1 (nucleotides 187 to 273 of SEQ ID NO:4; nucleotides 404 to 520 of SEQ ID NO:5) and 361 bp SAA2 (nucleotides 187 to 273 of SEQ ID NO:6; nucleotides 404 to 546 of SEQ ID NO:6) RT-PCR product sequences. The numbering refers to the full mRNA sequences. The intron exon boundary is marked with a vertical line, amplification from genomic DNA would generate a product that incorporates sequence encompassing the 384 bp (SAA1) or 394 bp (SAA2) intron at this position. The 3' UTRs are underlined once and the primer sequences are underlined twice. Diagonal lines represent 121 bases of aligned sequences which contain no gaps. Dashes represent regions of the SAA2

The above RT-PCR method was applied to total RNA from untreated and treated HepG2 cells. Products derived from SAA1 or SAA2 mRNA were not detected in untreated cells or following treatment with dexamethasone alone (FIG. 8B, lanes 1 and 2). However, the ratio of the levels of the SAA1 to SAA2 PCR products was approximately 2:5 following treatment with IL-1 and IL-6 (FIG. 8B, lane 3), indicating that the endogenous SAA2 gene has a significant transcriptional advantage (i.e., ~2.5 fold) when induced by cytokines in the absence of glucocorticoids. In contrast, the ratio of the levels of the SAA1 to SAA2 PCR products from cells treated with IL-1 and IL-6 plus dexamethasone was 5:4 (FIG. 8B, lane 4), indicating that the above cytokine driven transcriptional advantage of the SAA2 promoter is superceded by a modest SAA1 transcriptional advantage in the presence of glucocorticoids. Thus, the responses of the endogenous genes to different combinations of pro-inflammatory mediators paralleled those observed in experiments using isolated promoters to drive a quantifiable reporter, thereby establishing that the SAA1 GRE is functional when in its native genomic and cellular environment.

Example 3

Evaluation of the Glucocorticoid-Dependent Differential Transcriptional Activities of the SAA1 and SAA2 Genes for Use in Determining Steroid Responsiveness in Patients with Diseases that have an Inflammatory Component Inflammatory bowel diseases (IBDs) (e.g., Crohn's and ulcerative colitis) are often treated with steroids, the efficacy of which is variable, both ab initio and over time. The assay according to the invention, which is based on the ratio of SAA1 to SAA2 mRNAs, is a useful tool for predicting and/or assessing steroid responder status. The assay is used to determine whether subjects suffering from IBD, for example, fall into four general categories: (i) in remission (not currently taking steroids but may have taken steroids in the past; (ii) steroid refractory (still with active disease, despite at least four weeks of steroid treatment); (iii) steroid dependent (quiescent on high doses of steroids, but tending to flare up if steroids are withdrawn); or (iv) active disease (naïve with respect to steroid therapy or not having taken steroids for at least six months (e.g., due to previous lack of efficacy and/or side effects).

After informed consent has been given, patients' disease status is evaluated and a 10 ml blood sample and buccal swab (e.g., obtained by gently rubbing the inside of the cheek with a small brush) is obtained. Alternatively, a biopsy sample may be obtained according to standard methods. The blood sample may be taken according to methods known in the art, e.g., in a standard heparin or EDTA blood collection tube or a blood tube which is specially treated or supplemented with an RNA preservative solution that inhibits RNase activity or the like (e.g., a PAXgene™ Blood RNA Tube, Qiagen, Hilden, Germany). The buccal swab is taken using, for example, a CYTO-PAK CytoSoft™ brush (Medical Packages Corp., Camarillo, Calif.) and is placed on ice to avoid degradation of the mRNA, or into an RNA preservative solution to inhibit RNase activity or the like.

Proportional RT-PCR analysis to determine the ratio of SAA1 mRNA to SAA2 mRNA is then performed according to the method of Example 2. Data is analyzed to establish the extent to which particular SAA1:SAA2 ratios are associated with particular steroid response phenotypes. The assay may form the basis of a patient care strategy wherein the ratio of SAA1 mRNA to SAA2 mRNA in nucleated blood cells and/or buccal cells and/or biopsy sample and/or tissue sample is correlated with (i) current clinical response to steroid therapy, and/or (ii) past clinical response to steroid therapy, and/or (iii) future clinical response to steroid therapy.

EQUIVALENTS

The invention may be embodied in other specific forms without departing from the spirit or essential characteristics thereof. The foregoing embodiments are therefore to be considered in all respects illustrative rather than limiting of the invention described herein.

---

What is claimed is:

1. A method for determining steroid responsiveness in a subject, comprising
   determining the ratio of protein expression levels of serum amyloid A1 (SAA1) gene and serum amyloid A2 (SAA2) gene in a clinical sample from said subject and comparing said ratio to a predetermined control ratio,
   wherein said SAA1 gene is a steroid responsive gene and said SAA2 gene is a steroid non-responsive gene,
   wherein said control ratio is the ratio of protein expression levels of said SAA1 gene and said SAA2 gene in either a nonresponsive subject or in a responsive subject, and
   wherein said subject is steroid responsive if said ratio is higher than the control ratio for a non-responsive subject or is similar to the control ratio for a responsive subject.

2. The method according to claim 1, wherein said protein expression levels are determined using at least one of the methods selected from the group consisting of an ELISA assay, Western Blot, Mass Spectrophotometry, and Fluorescence Activated Cell Sorting.

3. The method according to claim 1, further comprising monitoring the steroid responsiveness over time to detect a change in responsiveness.

4. The method according to claim 1, further comprising administering to the sample at least one of the members selected from the group consisting of at least one pro-inflammatory mediator and at least one anti-inflammatory mediator.

5. The method according to claim 4, comprising administering tumor necrosis factor (TNF-α).

6. The method according to claim 4, comprising administering one or more anti-inflammatory mediators selected from the group consisting of interleukin 1 receptor antagonist (IL-1RA), tumor necrosis factor receptor antagonist (TNF-RA), soluble TNF receptors, anti-TNF antibodies, and anti-TNF-RA antibodies.

7. The method according to claim 1, further comprising the step of administering one or more cytokines, chemokines, interferons or hormones to said clinical sample.

8. The method according to claim 1, further comprising the step of administering a compound selected from the group consisting of interleukin-8 (IL-8) and vasoactive intestinal peptide (VIP).

9. The method according to claim 1, wherein said sample comprises a fluid selected from the group consisting of blood, serum, plasma, cerebrospinal fluid, ascites fluid, synovial fluid, fluid harvested from a site of inflammation, fluid harvested from a pooled collection site, saliva, semen and bronchial lavage.

10. The method according to claim 1, wherein said sample comprises nucleated cells.

11. The method according to claim 10, wherein said sample comprises cells selected from the group consisting of monocytes, macrophages, neutrophils, T-cells, B-cells, basophils, fibroblasts, endothelial cells and epithelial cells.

12. The method according to claim 1, wherein said sample comprises buccal cells.

13. A method for determining steroid responsiveness in a subject undergoing steroid treatment, comprising:
   comparing the protein expression level ratio of SAA1 gene and SAA2 gene in a clinical sample obtained from said subject prior to steroid administration with the expression level ratio of said SAA1 gene and said SAA2 gene in a clinical sample obtained from said subject after administration of a steroid,
   wherein said SAA1 gene is a steroid responsive gene and said SAA2 gene is a steroid non-responsive gene, and wherein a pre-administration ratio that is less than the post-administration ratio is indicative of steroid responsiveness in said subject, and
   wherein a pre-administration ratio that is greater than or the same as the post-administration ratio is indicative of steroid non-responsiveness in said subject.

14. A method for determining steroid responsiveness in a clinical sample, comprising:
   comparing the protein expression level ratio of SAA1 gene and SAA2 gene in said clinical sample obtained prior to in vitro exposure of said sample to a steroid with the protein expression level ratio of said SAA1 gene and said SAA2 gene in said clinical sample obtained after in vitro exposure of said sample to a steroid,
   wherein said SAA1 gene is a steroid responsive gene and said SAA2 gene is a steroid non-responsive gene, and wherein a pre-exposure ratio that is less than the post-exposure ratio is indicative of steroid responsiveness in said sample, and
   wherein a pre-exposure ratio that is greater than or the same as than the post-exposure ratio is indicative of steroid non-responsiveness in said sample.

* * * * *